US008669347B2

(12) United States Patent
Nemazanyy et al.

(10) Patent No.: US 8,669,347 B2
(45) Date of Patent: Mar. 11, 2014

(54) TRUNCATED VARIANT OF THE MAMMALIAN TARGET FOR RAPAMYCIN (MTOR) PROTEIN

(75) Inventors: Ivan Nemazanyy, London (GB); Ganna Panasyuk, London (GB); Alexander Zhyvoloup, Slough (GB); Michael Waterfield, London (GB); Ivan Gout, London (GB)

(73) Assignees: UCL Business PLC, London (GB); Ludwig Instituted for Cancer Research, New York, NY (US)

( * ) Notice: Subject to any disclaimer, the term of this patent is extended or adjusted under 35 U.S.C. 154(b) by 582 days.

(21) Appl. No.: 12/598,394

(22) PCT Filed: May 1, 2008

(86) PCT No.: PCT/GB2008/001548
§ 371 (c)(1),
(2), (4) Date: May 24, 2010

(87) PCT Pub. No.: WO2008/132494
PCT Pub. Date: Nov. 6, 2008

(65) Prior Publication Data
US 2010/0247542 A1 Sep. 30, 2010

Related U.S. Application Data

(60) Provisional application No. 60/924,145, filed on May 1, 2007.

(51) Int. Cl.
*C07K 14/00* (2006.01)

(52) U.S. Cl.
USPC .......................................... 530/352; 530/350

(58) Field of Classification Search
None
See application file for complete search history.

(56) References Cited

U.S. PATENT DOCUMENTS

| 6,830,909 B1 | 12/2004 | Gout et al. | |
|---|---|---|---|
| 2004/0253677 A1 | 12/2004 | Sabatini et al. | |
| 2005/0037344 A1* | 2/2005 | Stuhlmuller et al. | 435/6 |
| 2005/0108791 A1* | 5/2005 | Edgerton | 800/284 |

FOREIGN PATENT DOCUMENTS

| WO | WO 95/33052 | 12/1995 |
|---|---|---|
| WO | WO 98/08956 | 3/1998 |
| WO | WO 2006/052249 | 5/2006 |
| WO | WO 2007/019421 | 2/2007 |

OTHER PUBLICATIONS

Attwood (Science 290: 471-473, 2000).*
Skolnick et al. (Trends in Biotech. 18: 34-39, 2000).*
Do-Hyung Kim et al., "mTOR Interacts with Raptor to Form a Nutrient-Sensitive Complex that Signals to the Cell Growth Machinery," *Cell*, vol. 110, pp. 163-175, Jul. 2002.
Dario Alessi et al., "3-Phosphoinositide-dependent protein kinase 1 (PDK1) phosphorylates and activates the p70 S6 kinase in vivo and in vitro," *Current Biology*, vol. 8, No. 2, pp. 69-81, Dec. 1997.
Nicholas Pullen et al., "The modular phosphorylation and activation of $p70^{S6K}$," *FEBS Letters 410*, pp. 78-82, 1997.
Christopher G. Proud, "p70 S6 kinase: an enigma with variations," *Trends Biochem.Science*, vol. 21, pp. 181-185, May 1996.
Huang et al., Targeting mTOR Signaling for Cancer Therapy, *Current Opinion in Pharmacology*, vol. 3, No. 4, pp. 371-377, Aug. 2003.
Heidi A. Lane, "A Review of the Potential of mTOR Inhibitors for the Treatment of Human Cancer," *Proceedings of the American Assoc. for Cancer Research Annual Meeting*, vol. 48., pp. 1373-1374, Apr. 2007.
"International Search Report and the Written Opinion of the International Searching Authority" International Application No. PCT/GB2008/001548, dated Sep. 17, 2008, pp. 1-15.
Song et al., "Novel roles of Akt and mTOR in suppressing TGF-β/ALK5-mediated Smad3 activation", *EMBO Journal*, 25, 58-69 (2006).

* cited by examiner

*Primary Examiner* — Sharon Wen
(74) *Attorney, Agent, or Firm* — Viksnins Harris & Padys PLLP

(57) ABSTRACT

The invention relates to mTORbeta, a splice form of mTOR, nucleic acids encoding mTOR beta, and antibodies against mTOR beta. The invention also relates to methods of producing mTOR beta and methods of screening for an agent that modulates mTOR beta expression and/or activity. The invention further relates to a method of treating a disease associated with aberrant expression of mTOR beta by administration of an agent that alters mTOR activity and/or expression.

1 Claim, 12 Drawing Sheets

A

B

TRUNCATED VARIANT OF THE MAMMALIAN TARGET FOR RAPAMYCIN (MTOR) PROTEIN

RELATED APPLICATION

This application claims priority to U.S. Provisional Application No. 60/924,145 that was filed on May 1, 2007.

FIELD OF THE INVENTION

The present invention relates to a truncated variant of the mammalian target for rapamycin (mTOR) protein.

BACKGROUND OF THE INVENTION

The mammalian target of rapamycin (mTOR) is a serine/threonine kinase, which belongs to a large family of PI3K-related kinases, which also includes DNA-dependent protein kinase, ATM and ATR. Biochemical and genetic studies demonstrated that mTOR integrates growth factor stimulation, energy, and nutrient availability to regulate biosynthetic processes responsible for cell growth, size, and cell cycle progression. The regulation of mTOR kinase activity in response to various extracellular cues has been extensively studied in the last decade. A whole range of cellular proteins with various enzymatic activities, scaffold and adaptor functions have been implicated in signaling to and regulating the activity of mTOR, including protein kinases PKB/Akt and AMPK, tumor suppressors PTEN and tuberous sclerosis complex TSC1/2, small GTP-binding protein Rheb, scaffolding proteins Raptor and Rictor. In an activated state, mTOR transduces signaling and metabolic information by phosphorylating major downstream targets, such as S6Ks, 4E-BP1 and PKB/Akt. Studies from various laboratories indicated that mTOR exists in two functionally distinct complexes, termed mTOR complex 1 (mTORC1) and mTORC2. The mTORC1 contains the core components mTOR, raptor, and mLST8/GβL, and is sensitive to rapamycin. The mTORC2 is believed to be rapamycin insensitive and contains mTOR, Rictor, and mLST8/GβL. Rapamycin and its analogues are currently evaluated as anticancer drugs in a number of clinical trials. In addition, they are now widely used for coating stents to reduce post-stenting restenosis after coronary angioplasty. In contrast to yeasts, which have two TOR genes, mammals possess only one gene, known to encode a single polypeptide with molecular weight of approximately 280 kDa.

One important downstream target of mTOR is S6K. S6 kinase (p70 S6 kinase ($p70^{S6k}$)) is responsible for S6 phosphorylation of the ribosomal S6 protein, which is a component of the 40S subunit of eukaryotic ribosomes (i.e., the cellular machinery responsible for translation of mRNA and protein synthesis). It is also believed to be the major physiological S6 kinase in mammalian cells (Proud, 1996 Trends Biochem. Sci. 21:181-185). The 40S ribosomal protein S6 is a component of the 40S subunit of eukaryotic ribosomes. The S6 protein is phosphorylated in response to certain cellular signaling events such as hormone or growth factor induced cellular proliferation.

S6 Kinase is activated by a variety of growth factors such as insulin, and mitogens (Alessi et al., 1998 Curr. Biol. 8:69-81). Certain drugs that regulate S6 kinase activity have been identified including rapamycin, which is the most potent inhibitor of S6 kinase (Pullen et al., 1997 FEBS Letters 410:78-82). The structure of and some functions of S6 kinase alpha and S6 kinase beta are disclosed in U.S. Pat. No. 6,830,909, herein incorporated by reference in its entirety.

S6 kinase has been shown to be both phosphorylated and acetylated. It was found that S6 kinase protein is acetylated both in vivo and in vitro by p300 and P/CAF acetyltransferases. More accurate to say that in conditions under which S6K acetylation is increased (i.e., presence of HDAC inhibitors/overexpression of p300), S6 kinase activity and 412 phosphorylation are reduced. Mutation of the P-loop lysines (which are acetylated by p300 in vitro) to glutamine, which mimics acetylation, results in the complete inactivation of S6Ks and loss of 412 phosphorylation. S6K2 (S6K beta) has also been shown to possesses an AT-hook DNA binding motif. Thus, S6 kinase 2 protein binds to DNA and is thereby activated which in turn stimulates its kinase activity. Therefore, S6K2 is thought to transduce growth-promoting effects in response to mitogens and nutrients. This may involve the regulation of transcription factors and/or chromatin remodeling proteins by phosphorylation, when S6K2 complexes with DNA and is activated by this interaction. Regulation of S6 Kinase protein activity and related methods are disclosed in WO 2007/019421, incorporated herein by reference in its entirety.

SUMMARY OF THE INVENTION

The present invention relates to a newly discovered splice form of mTOR, called mTOR beta (mTORβ). In particular, the invention provides an isolated polypeptide which phosphorylates S6K1 and/or 4E-BP1 selected from the group consisting of:
(a) an isolated polypeptide comprising the amino acid sequence of SEQ ID NO: 2;
(b) an isolated polypeptide comprising an amino acid sequence having at least 75% sequence identity with the amino acid sequence of SEQ ID NO: 2; and
(c) an isolated polypeptide comprising the amino acid sequence encoded by SEQ ID NO: 1.

The invention also provides:
An isolated polynucleotide selected from the group consisting of:
(a) a polynucleotide encoding a polypeptide of the invention;
(b) a polynucleotide comprising the nucleotide sequence of SEQ ID NO: 1 or the complement thereof;
(c) a polynucleotide comprising a nucleic acid sequence having at least 80% sequence identity over the entire contiguous sequence of SEQ ID NO: 1 and encoding a protein that phosphorylates S6K1 and/or 4E-BP1; and
(d) an isolated nucleic acid molecule which hybridizes to the nucleotide sequence of SEQ ID NO: 1 or the complement thereof under conditions which employ 0.1×SSC at 68° C. and encoding a protein which phosphorylates S6K1 and/or 4E-BP1.

A vector comprising a polynucleotide of the invention.

A host cell comprising a polypeptide of the invention, a polynucleotide of the invention or a vector of the invention.

An isolated antibody that specifically binds to a polypeptide of the invention.

A method for producing a polypeptide comprising culturing a host cell of the invention under conditions in which a polypeptide of the invention or a polypeptide encoded by a polynucleotide of the invention is expressed.

A method of screening for an agent that modulates mTOR-beta activity, comprising the following steps:
(a) contacting a polypeptide of the invention with a test agent; and
(b) detecting any change in the activity of said polypeptide, wherein a change in activity is indicative of an agent capable of modulating mTORbeta activity.

A method of screening for an agent that modulates mTOR-beta expression and/or activity, comprising the following steps:
(a) providing a host cell according to claim 5 that comprises or expresses a polypeptide of the invention or a polypeptide encoded by a polynucleotide of the invention;
(b) contacting said host cell with a test agent; and
(c) detecting any change in the expression and/or activity of said polypeptide,
wherein a change in expression and/or activity is indicative of an agent capable of modulating mTORbeta expression and/or activity.

A method of treating a disease associated with aberrant expression of a polypeptide of the invention comprising administration of an effective amount of an agent to a subject in need thereof, wherein said agent alters the activity and/or expression of said polypeptide.

An agent that alters activity and/or expression of a polypeptide of the invention for use in the treatment of a disease associated with aberrant expression of said polypeptide.

BRIEF DESCRIPTION OF THE DRAWINGS

FIG. 4A shows agarose gels for the total RNA and mTOR beta RNA from Hep2G, HEK293, and MCF7. Total RNA was purified from Hep2G, HEK293 and MCF7 cell lines and converted into first strand DNAs. A set of mTOR specific primers was used in PCR reactions to search for potential splice variants. Amplified fragments were resolved by electrophoresis in 2% agarose gel. The most prominent bands were excised from the gel and sequence analyzed. One set of primers (N1 and C3) consistently amplified a 100 bp fragment from three cell lines. Specific fragments of glyceraldehyde-3-phosphate dehydrogenase (GADPH) and β-actin were amplified and used as loading and quality controls of first strand DNA. FIG. 4B shows the sequence alignment of 100 bp PCR fragments, amplified with N1 and C3 mTOR specific primers. Amplified fragments were sequenced and aligned by Clustal W program. The position of the potential splice fusion is indicated by an arrow. FIG. 4C shows the amino acid sequence of a 100 bp PCR product, amplified with N1 and C3 mTOR specific primers. The arrow indicates the position of a potential splice fusion. The sequences, corresponding to the N-terminal region and the FATN domain of mTOR are underlined.

FIG. 6A shows a gel of cells expressing mTORβ upon transfection with pcDNA 3.1 mTORβ. HEK293 cells were transfected with pcDNA3.1 or pcDNA 3.1 mTORβ. One day later, cells were starved for 24 hours and than stimulated with 10% fetal bovine serum for 1 hour. Rapamycin (10 nM) was added 30 minutes before stimulation. Cells were lysed, resolved by SDS-PAGE and immunoblotted with the C-terminal anti-mTOR and pS2448 mTOR antibodies. FIG. 6B shows the results of the mTOR in vitro kinase assay. HEK293 cells were transfected with pcDNA3.1, pcDNA 3.1/FLAG-mTORβ or pcDNA 3.1/FLAG-mTORa. Two days later, cells were lysed and immunoprecipitated with anti-FLAG antibody. The immune complexes were used in mTOR in vitro kinase assay with His-4E-BP1 and His-S6K1C as substrates. Kinase reactions were resolved by SDS-PAGE and immunoblotted with phosphospecific antibodies to 4E-BP1 p65 and S6K1 p389. The level of immunoprecipitated FLAG-mTORα and FLAG-mTORβ was measured by Western blotting with anti-FLAG.

BRIEF DESCRIPTION OF THE SEQUENCE LISTING

Figure 1:
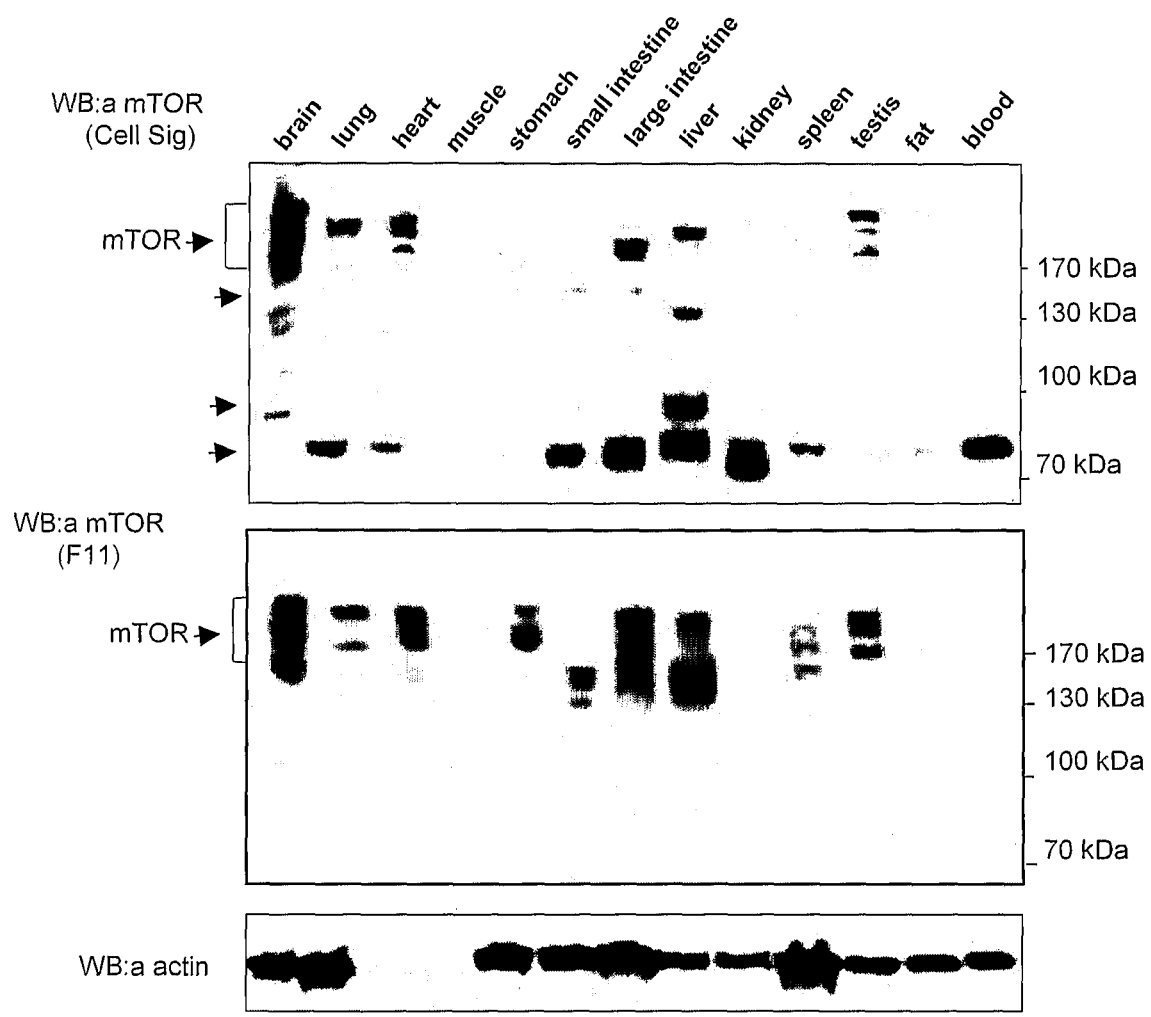
FIG. 1 shows a Western blot analysis of mTOR expression in rat tissues using the C-terminal and F11 anti-mTOR antibodies. Protein extracts (30 μg) of rat tissues were resolved by SDS-PAGE, transferred to a PVDF membrane, and probed with the C-terminal mTOR polyclonal antibodies from Cell Signaling (upper panel). The membrane was then stripped and reprobed with anti-actin antibodies (lower panel).

SEQ ID NO: 1 is the polynucleotide sequence encoding the human mTOR beta splice variant and SEQ ID NO: 2 is the amino acid sequence of the human mTOR beta protein.

SEQ ID NO: 3 is the polynucleotide sequence encoding the full-length human mTOR alpha protein and SEQ ID NO: 4 is the amino acid sequence of the human mTOR alpha protein.

SEQ ID Nos 5 to 8 are the primers used in Example 4.

SEQ ID NO: 9 is an amplified fragment produced by PCR from human MCF7, Keh293 and HEP2G cell lines and SEQ ID NO: 10 is the amino acid sequence encoded by SEQ ID NO: 9.

DETAILED DESCRIPTION OF THE INVENTION

The present invention is based on the identification and characterization of a new splice form of the mammalian target for rapamycin (mTOR) protein. This is the first time that the existence of a new splice form (termed herein after mTOR beta or mTORβ) of mTOR has been shown. The present invention is based on assays for the mTOR beta protein and studies of its activity.

It has been determined that mTOR beta is a splice fusion of N-terminal amino acids 1 to 23 and the C-terminal amino acids 1867 to 2549 of the currently known mTOR (hereinafter mTORα), which produces a fusion protein 706 amino acids in length (SEQ ID NO: 2). In the fusion protein, the regulatory HEAT and FAT domains are lost. It has also been shown that mRNA transcripts corresponding to mTORβ are highly expressed in heart and liver, while kidney, liver, blood, small, and large intestine have the highest protein level of mTORβ. Furthermore, similarly to the full-length mTORα, the splice form is also capable to associate with substrate-presenting molecules Raptor, Rictor, and GβL. mTORβ can also phosphorylate S6K1 and 4E-BP1 in vitro. In addition, it was shown that mTORβ is phosphorylated at a serine residue corresponding to Ser2448 (S2448) of the entire mTORα amino acid sequence (Ser605 of mTORβ) in response to serum stimulation. Phosphorylation of mTORβ at a serine residue corresponding to Ser2448 of the entire mTORα amino acid sequence is sensitive to Rapamycin. Also, it was shown that when compared to mTORα, mTORβ is less sensitive to Rapamycin.

As used herein, the term "mTOR beta" (mTORβ) refers to the splice-form of mTOR. For example, the inventors have found that the polypeptide of SEQ ID NO: 2 is a naturally occurring human mTOR beta polypeptide. This protein is thought to be 706 amino acids in length and is encoded by a nucleic acid of SEQ ID NO: 1, approximately 2121 nucleotides in length. As used herein, the term "mTOR alpha" (mTORα) refers to full-length mammalian target for rapamycin (mTOR) protein. For example, the human mTOR alpha polypeptide is thought to be a protein approximately 2549 amino acids in length (SEQ ID NO: 4) and is thought to be encoded by a nucleotide of SEQ ID NO: 3.

Polypeptides

The present invention provides mTOR beta polypeptides.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including glycine and both the D or L optical isomers, and amino acid analogs and peptidomimetics.

The polypeptides of the present invention are preferably provided in isolated form. As used herein, a protein is said to be isolated when physical, mechanical, or chemical methods are employed to remove the protein from cellular constituents that are normally associated with the protein. A skilled artisan can readily employ standard purification methods to obtain an isolated protein.

The present invention includes mTOR beta (mTORβ) polypeptides. An mTOR beta polypeptide according to the invention may be a naturally occurring mTOR beta polypeptide, or may be a variant, derivative or fragment thereof as described herein. In one embodiment of the invention, an mTOR beta polypeptide consists of, consists essentially of or comprises the amino acid sequence of SEQ ID NO: 2. In one embodiment of the invention, an mTOR beta polypeptide is a splice fusion between N-terminal amino acids 1 to 23 and the C-terminal amino acids 1867 to 2549 of mTORα, such as those amino acids in the mTORα polypeptide of SEQ ID NO: 4. In another embodiment of the invention, the mTOR beta polypeptide consists of, consists essentially of or comprises a sequence having at least 75% or at least 95% sequence identity with the amino acid sequence of SEQ ID NO: 2 and phosphorylates S6K1 and/or 4E-BP1.

A polypeptide of the invention may be encoded by a polynucleotide of the invention as described herein, such as by the nucleotide sequence of SEQ ID NO: 1 or by a polynucleotide comprising SEQ ID NO: 1. A polypeptide of the invention may be encoded by a polynucleotide having at least 80% or at least 95% sequence identity over the entire contiguous sequence of SEQ ID NO: 1, or by a polynucleotide that hybridizes to the polynucleotide of SEQ ID NO: 1 under conditions that employ 0.1×SSC at 68° C. The polypeptide encoded by such polynucleotides will be capable of phosphorylating S6K1 and/or 4E-BP1.

The mTOR beta polypeptide may be a naturally occurring mTOR beta polypeptide or a variant, derivative or fragment thereof. The naturally occurring mTOR beta polypeptide may be an mTOR beta polypeptide that is naturally expressed in any species, preferably a mammalian species. For example, a suitable naturally occurring mTOR beta polypeptide may be a mammalian mTOR beta polypeptide from a human, a non-human primate, a rodent (e.g. rat or mouse), a rabbit, a horse, or a livestock animal (e.g. a goat, sheep, pig or cow). The mTOR beta polypeptide may be a rabbit, mouse, rat, porcine, bovine, ovine, equine, human or non-human primate mTORβ polypeptide. Preferably, the mTOR beta polypeptide is a human mTOR beta polypeptide. For example, the amino acid sequence of a human mTOR beta polypeptide is given in SEQ ID NO: 2. The polynucleotide sequence encoding a human mTOR beta polypeptide is given in SEQ ID NO: 1. An mTOR beta polypeptide according to the invention may be any such naturally occurring mTOR beta polypeptide, such as a human polypeptide, or may be an allelic variant thereof. Allelic variants, though possessing a slightly different amino acid sequence than those recited above, will still have the same or similar biological functions associated with the disclosed protein.

The mTOR beta polypeptide may be a variant polypeptide, such as a derivative, analog, polypeptide fragment or mimetic of a naturally occurring mTOR beta peptide. Such a variant polypeptide preferably retains the same biological function or activity as a naturally occurring mTOR beta peptide. The activity may be any activity possessed by a naturally occurring mTOR beta polypeptide. A number of activities of mTOR beta are disclosed herein. A suitable variant polypeptide may have any one or more of these activities. For example, a variant polypeptide may retain the ability to be acetylated and/or the ability to phosphorylate second proteins and/or the ability to bind DNA. For example, a suitable variant polypeptide may induce cMyc impression. A suitable variant polypeptide may be phosphorylated at a serine residue corresponding to S2448 of the entire mTORα amino acid sequence of SEQ ID NO: 4 (Ser605 of the mTORβ polypeptide of SEQ ID NO: 2). A suitable variant polypeptide may have the ability to phosphorylate S6K1. A suitable variant polypeptide may have the ability to phosphorylate 4E-BP1. A suitable variant polypeptide may have the ability to phosphorylate S6K1 and 4E-BP1. A suitable variant polypeptide may interact with one, two, or all three of Raptor, Rictor and GβL. A suitable variant polypeptide may induce cell proliferation. A suitable variant polypeptide may protect cells from starvation-induced cell death. A suitable variant polypeptide may increase the oncogenic potential of a cell. A suitable variant polypeptide may decrease the length of the G1 phase of the cell cycle. Methods for assessing these activities are described herein and would be readily understood by the skilled reader. The Examples show how such activities may be assessed and use the polypeptide of SEQ ID NO: 2 as an example. These methods could be readily adapted for use with other polypeptides as described herein.

An mTORβ polypeptide of the invention may retain one or more functions of a full length mTORα polypeptide. These functions may include one or more of: kinase activity; activations through the phosphorylation of a serine residue corresponding to S2448 of the mTORα amino acid sequence of SEQ ID NO: 4 (Ser605 of the mTORβ polypeptide of SEQ ID NO: 2); the ability to phosphorylate other proteins, such as the ability to phosphorylate S6K1 and/or the ability to phosphorylate 4E-BP1; the ability to interact with, or bind to, one, two, or all three of Raptor, Rictor and GβL.

An mTOR beta polypeptide of the invention may retain at least one activity of naturally occurring mTOR beta that is different to that of full length mTOR alpha polypeptide. For example, as described herein, cells expressing mTORβ proliferate faster than cells expressing mTORα; expression of mTORβ, but not mTORα, leads to induction of c-Myc protein expression; cells expressing mTORβ have a shorter duration of G1 phase than cells expressing mTORα; expression of mTORβ, but not mTORα, protects cells against the effects of serum starvation; expression of mTORβ leads to an increase in cell oncogenic potential compared to cells expressing mTORα. An mTORβ polypeptide of the invention may retain any one or more of these differences when compared to an mTORα polypeptide.

Polypeptide variants include, but are not limited to, deletion, addition or substitution variants of a naturally occurring mTORβ polypeptide such as the polypeptide of SEQ ID NO: 2. For example, a suitable variant may be a substitution, deletion or addition variant of such a sequence or may be a fragment of any such sequence. A variant polypeptide may comprise 1, 2, 3, 4, 5, up to 10, up to 20, up to 30, up to 40, up to 50, up to 75 or more amino acid substitutions and/or deletions from a naturally occurring mTORβ polypeptide sequence, such as from SEQ ID NO: 2.

"Substitution" variants preferably involve the replacement of one or more amino acids with the same number of amino acids and making conservative amino acid substitutions. A polypeptide may have conservative substitution of one or more amino acids with one or more other amino acids. One skilled in the art is aware that various amino acids have similar characteristics. One or more such amino acids of a polypeptide can often be substituted by one or more other such amino acids without eliminating a desired property of that polypeptide (such as acetyltransferase activity). For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |

| | | | |
|---|---|---|---|
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

For example, the amino acids glycine, alanine, valine, leucine, and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids that can often be substituted for one another include phenylalanine, tyrosine and tryptophan (amino acids having aromatic side chains), lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

As used herein, a conservative variant refers to alterations in the amino acid sequence that do not adversely affect a biological function or activity of the protein such as a function/activity as described above. For example, conservative variants may retain their ability to be acetylated, the ability to phosphorylate second proteins and the ability to bind DNA. A substitution, insertion, or deletion is said to adversely affect the protein when the altered sequence prevents or disrupts a biological function or activity associated with the protein. For example, the overall charge, structure, or hydrophobic/hydrophilic properties of the protein can be altered without adversely affecting a biological activity. Accordingly, the amino acid sequence can be altered, for example to render the polypeptide more hydrophobic or hydrophilic, without adversely affecting the biological activities of the protein.

Variant polypeptides may have an amino acid sequence having at least about 75% amino acid sequence identity with a naturally occurring mTORβ polypeptide sequence, such as with the entire sequence set forth in SEQ ID NO: 2, more preferably at least about 80%, at least about 90%, at least about 95%, at least about 97%, and most preferably at least about 99% sequence identity. For example, human, mouse and rat TOR share 95% identity on the protein level. Any of these levels of amino acid identity may be present across the full length of the naturally occurring mTORβ polypeptide sequence, or may be present across a subsection of the full length sequence, such as across 50, 100, 150, 200 or more amino acids thereof. Any of these levels of amino acid identity may be present across the full contiguous mTORβ polypeptide sequence. The level of sequence identity may vary in different regions of the mTORβ sequence. For example, a variant mTORβ may have at least 75% amino acid identity across the full length of a naturally occurring mTORβ polypeptide, but may have a higher level of sequence identity within some regions. For example, such a variant polypeptide may retain one or more conserved domains from the naturally occurring sequence.

Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. Fusion proteins, or N-terminal, C-terminal or internal extensions, deletions, or insertions into the polypeptide sequence shall not be construed as affecting homology.

In connection with amino acid sequences, "sequence identity" refers to sequences which have the stated value when assessed using ClustalW (Thompson et al., 1994, supra) with the following parameters: Pairwise alignment parameters—Method: accurate, Matrix: PAM, Gap open penalty: 10.00, Gap extension penalty: 0.10; Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

Preferred "derivatives" or "variants" include those in which instead of the naturally occurring amino acid the amino acid which appears in the sequence is a structural analog thereof. Amino acids used in the sequences may also be derivatized or modified, e.g. labelled, providing the function of the peptide is not significantly adversely affected.

Derivatives and variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

Deletion and insertion variants of the polypeptides are within the scope of the present invention. Amino acid deletions can be advantageous since the overall length and the molecular weight of a polypeptide can be reduced whilst retaining a desired activity. This can enable the amount of polypeptide required for a particular purpose to be reduced. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. Amino acid insertions relative to a polypeptide can also be made. This may be done to alter the nature of the polypeptide (e.g., to assist in identification, purification or expression). Polypeptides incorporating amino acid changes (whether substitutions, deletions or insertions) relative to the sequence of a polypeptide as defined above can be provided using any suitable techniques. For example, a nucleic acid sequence incorporating a desired sequence change can be provided by site-directed mutagenesis. This can then be used to allow the expression of a polypeptide having a corresponding change in its amino acid sequence.

The polypeptides of the present invention include naturally occurring mTORβ molecules, such as the polynucleotide having the amino acid sequence disclosed in SEQ ID NO: 2, and amino acid sequence variants of any thereof wherein one or more amino acid residues has been inserted N- or C-terminal to, or within, the disclosed coding sequence. As explained above, the mTORβ polypeptide of SEQ ID NO: 2 is formed by splicing together two fragments from a full length mTORα polypeptide. SEQ ID NO: 2 thus comprises amino acids 1 to 23 and 1867-1549 of SEQ ID NO: 4. A variant mTORβ may comprise the equivalent fragments from another mTORα polypeptide, such as for another naturally occurring mTORα polypeptide. The equivalent amino acids in a related polypeptide may be readily identified by, for example, sequence alignment and comparison. A variant mTORβ may thus be formed by combining an N terminal fragment and a C terminal fragment from a naturally occurring mTORα polypeptide. A variant mTORβ polypeptide may also vary in sequence from such N and C terminal fragments. For example, a variant mTORβ polypeptide may have any of the degrees of amino acid sequence identity discussed above when compared to the relevant N and C terminal fragments from any naturally occurring mTORα polypeptide.

A variant mTORβ may comprise different fragments from an mTORα polypeptide that can be spliced together to form a polypeptide having mTORβ activity as defined above.

Using the mTORα polypeptide of SEQ ID NO: 4 as an example, the mTORβ polypeptide of the invention may comprise amino acids 1 to 23 of SEQ ID NO: 4, or may comprise more or fewer amino acids from the N-terminal of mTORα. A suitable fragment of mTORα may start from residue 1 of SEQ ID NO; 4 or may start from a subsequent residue, such as amino acid 2, 3, 4, 5, 6 or a later amino acid. A suitable fragment of mTORα may end at residue 23 of SEQ ID NO: 4 or may end at a different residue such as amino acid 18, 19, 20, 21, 22, 24, 25, 26, 27 or 28 or an earlier or later amino acid residue. Any combination of these start and end points may be used to form a suitable fragment. A suitable fragment from the N terminal of mTORα may be, for example, 15, 17, 18, 20, 21, 22, 23, 24, 25, 27, 30, 35 or more amino acids in length.

Similarly, the mTORβ polypeptide may comprise amino acids 1867-2549 of SEQ ID NO: 4, or may comprise more or fewer amino acids from the C-terminal of mTORα. A suitable fragment of mTORα may start from residue 1867 of SEQ ID NO; 4 or may start from a different residue, such as amino acid 1860, 1861, 1862, 1863, 1864, 1865, 1866, 1868, 1869, 1870, 1871, 1872, 1873 or an earlier or later amino acid. A suitable fragment of mTORα may end at residue 2549 of SEQ ID NO: 4 or may end at an earlier residue such as amino acid 2548, 2547, 2546, 2545, 2544 or an earlier amino acid residue. However, it is preferred that the C-terminal fragment of mTORα includes the FATC domain located at amino acids 2517 to 2549 of SEQ ID NO: 4. Any combination of these start and end points may be used to form a suitable fragment. A suitable fragment from the C terminal of mTORα may be, for example, up to 680, 681, 682, 683, 684, 685, 686, 690, 695, 700 or more amino acids in length.

The mTORβ polypeptide may comprise any combination of such N-terminal and C-terminal fragments from an mTORα polypeptide. Such fragments may be further modified from a naturally occurring sequence by substitution, addition or deletion as described herein.

Figure 5:
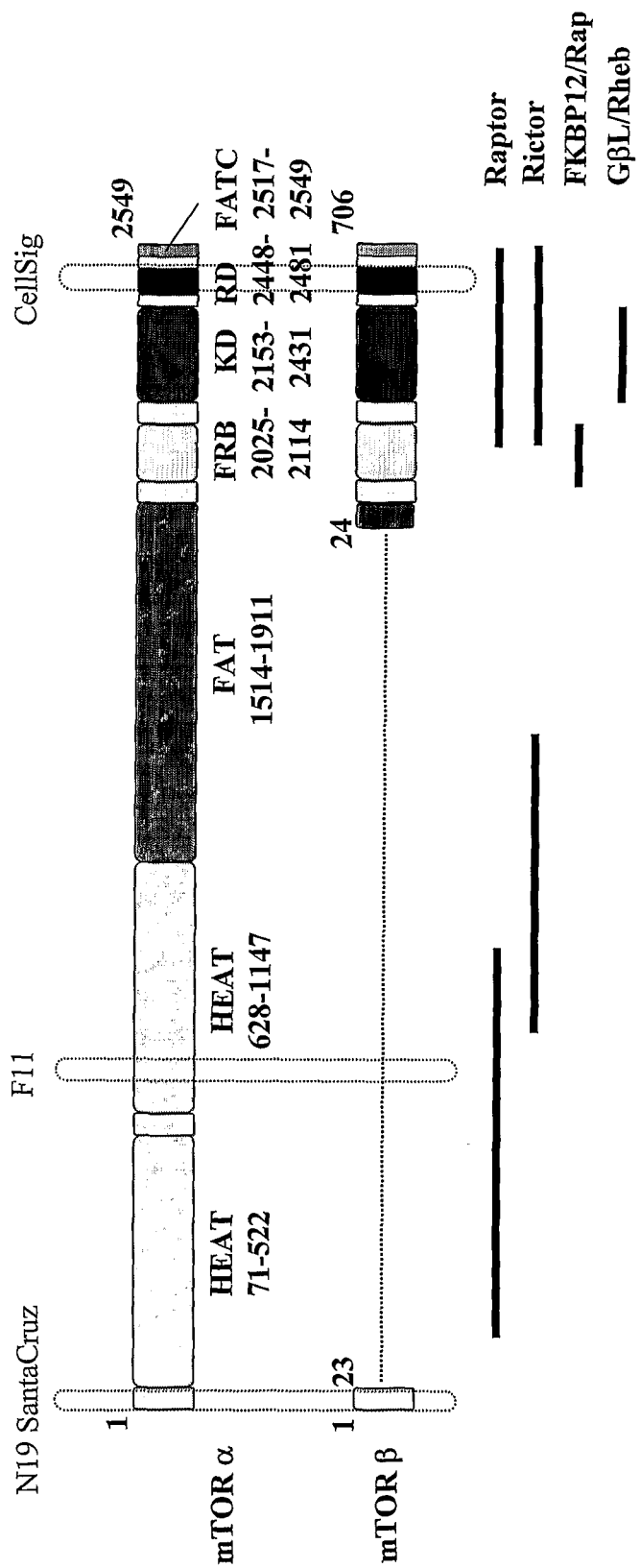
FIG. 5 shows the domain organization of the full-length mTORα and mTORβ splicing isoform. The location of each domain, including its amino acid position, is indicated. The localization of the epitopes, corresponding to anti-mTOR antibodies is indicated. Regions mediating the interaction of known mTOR binding partners are underlined. There are 20 HEAT motifs (Huntingtin, EF3, A subunit of PP2A and Tor) of 37-43 amino acids each which are implicated in protein-protein interactions. HEAT18 and 19 are sufficient to target mTOR to the ER or Golgi. mTOR dimerizes via these HEAT regions. FAT domain=FRAP/ATM/TRAPP; FATN=FAT domain at N-terminus; FATC=FAT domain at C-terminus. The FATC domain was found to be necessary for mTOR kinase activity and function. FRB (FKBP12-rapamycin binding) domain is a conserved 11 kDa region necessary and sufficient for FKBP12-rapamycin binding. KD=kinase domain, believed to be a PI3K-related domain. RD=regulatory domain.

As described above, the mTORβ polypeptide will retain at least one function/activity of mTORβ, such as at least one function/activity of mTORα. As shown in FIG. 5, the mTORβ of SEQ ID NO: 2 retains certain domain from mTORα, but lacks others. For example, the mTORβ of SEQ ID NO: 2 lacks the regulatory HEAT and FATN domains from mTORα. It therefore appears that these domains are unnecessary for the function for mTORβ. The mTORβ polypeptide may therefore lack one, more or all HEAT domains from an mTORα polypeptide. The mTORβ may completely lack functional HEAT domains. The mTORβ polypeptide may lack the FATN domain from an mTORα polypeptide. The mTORβ polypeptide may lack a functional FAT domain.

The mTORβ polypeptide of SEQ ID NO:2 does, however, retain other domains from mTORα. Amino acids or structural features from these domains may be responsible for the various activities of mTORβ. The mTORβ polypeptide may therefore retain an FRB domain and/or a kinase domain (KD) and/or a regulatory domain and/or an FATC domain. The FRB domain is necessary and sufficient for FKBP12-rapamycin binding. The mTORβ polypeptide may retain an FRB domain. The mTORβ polypeptide may retain an alternative or variant domain that confers FKBP12-rapamycin binding ability. The kinase domain is a P13 kinase-related domain. The mTORβ polypeptide may retain a kinase domain. The mTORβ polypeptide may retain an alternative or variant domain that confers P13 kinase ability. The FATC domain is necessary for mTOR kinase activity and function. The mTORβ polypeptide may retain an FATC domain. The mTORβ polypeptide may retain an alternative or variant domain that confers such mTORβ kinase activity and function. The mTORβ polypeptide may retain two or more of these domains from mTORα, such as both a kinase domain and an FATC domain. The mTORβ polypeptide may also retain functional binding sites for Raptor and/or Rictor and/or GβL.

The polypeptides of the invention also include naturally occurring mTORβ molecules such as the polynucleotide having the amino acid sequence disclosed in SEQ ID NO: 2 and amino acid sequence variants of the disclosed sequence, or their fragments as defined above, that have been substituted by at least one residue. Such fragments, also referred to as peptides or polypeptides, may contain functional regions of the protein identified as regions of the amino acid sequence which correspond to known protein domains, such as the AT-hook domain, as well as regions of pronounced hydrophilicity. The regions are all easily identifiable by using commonly available protein sequence analysis software such as MacVector (Oxford Molecular).

Polypeptide "fragments" according to the invention may be made by truncation, e.g. by removal of one or more amino acids from the N and/or C-terminal ends of a polypeptide. Up to 10, up to 20, up to 30, up to 40, up to 50, up to 60, up to 75 or more amino acids may be removed from the N and/or C terminal in this way. Fragments may also be generated by one or more internal deletions.

A polypeptide of the invention may comprise further additional sequences, for example those encoded by the polynucleotides and vectors described below. The polypeptide may comprise a leader sequence, i.e. a sequence at or near the amino terminus of the polypeptide that functions in targeting or regulation of the polypeptide. For example a sequence may be included in the polypeptide that targets it to particular tissues in the body, or which helps the processing or folding of the polypeptide upon expression. Various such sequences are well known in the art and could be selected by the skilled reader depending upon, for example, the desired properties and production method of the polypeptide.

A polypeptide may further comprise a tag or label to identify or screen for the polypeptide, or for expression of the polypeptide. Suitable labels include radioisotopes such as $^{125}I$, $^{32}P$ or $^{35}S$, fluorescent labels, enzyme labels, or other protein labels such as biotin. Suitable tags may be short amino acid sequences that can be identified by routine screening methods. For example, a short amino acid sequence may be included that is recognised by a particular monoclonal antibody.

Polypeptides of the invention, as defined herein, may be chemically modified, for example, post-translationally modified. For example they may be glycosylated or comprise modified amino acid residues. They can be in a variety of forms of polypeptide derivatives, including amides and conjugates with polypeptides.

Chemically modified peptides also include those having one or more residues chemically derivatized by reaction of a functional side group. Such derivatized side groups include those which have been derivatized to form amine hydrochlorides, p-toluene sulfonyl groups, carbobenzoxy groups, t-butyloxycarbonyl groups, chloroacetyl groups and formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Peptides may also be modified by phosphorylation, for example 3 amino phosphorylation and by glycosylation for example mannosylation.

Also included as chemically modified peptides are those which contain one or more naturally occurring amino acid derivatives of the twenty standard amino acids. For example, 4-hydroxyproline may be substituted for proline or homoserine may be substituted for serine.

Contemplated variants of polypeptides containing and/or derivatives further include those containing predetermined mutations by, e.g., homologous recombination, site-directed or PCR mutagenesis, and the corresponding proteins of other animal species, including but not limited to rabbit, mouse, rat, porcine, bovine, ovine, equine and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

mTOR beta Peptide Mimics

Peptide mimetics may be produced that mimic the three-dimensional structure of mTORβ. Such peptide mimetics may have significant advantages over naturally occurring peptides including, for example, more economical production, greater chemical stability, enhanced pharmacological properties (half-life, absorption, potency, efficacy, etc.), altered specificity (e.g., a broad-spectrum of biological activities), reduced antigenicity and others.

Such mimetics may have any open or more of the functions or activities of mTORβ discussed above. In one form, mimetics are peptide-containing molecules that mimic elements of mTORβ secondary structure. In another embodiment, the mimetics are capable of binding to cMyc. In an alternate embodiment, the mimetics are able to bind with any one of Raptor, Rictor, and GβL. In yet another embodiment, the mimetics are able to phosphorylate S6K1 and/or 4E-BP1.

The underlying rationale behind the use of peptide mimetics is that the peptide backbone of proteins exists chiefly to orient amino acid side chains in such a way as to facilitate molecular interactions, similar to those of antibody and antigen. A peptide mimetic is expected to permit molecular interactions similar to the natural molecule. In another form, peptide analogs are commonly produced in the pharmaceutical industry as non-peptide drugs with properties analogous to those of the template peptide. These types of non-peptide compounds are also referred to as peptide mimetics or peptidomimetics (Fauchere (1986) Adv. Drug Res. 15, 29-69; Veber & Freidinger (1985) Trends Neurosci. 8, 392-396; Evans et al. (1987) J. Med. Chem. 30, 1229-1239 which are incorporated herein by reference) and are usually developed with the aid of computerized molecular modeling.

Peptide mimetics that are structurally similar to therapeutically useful peptides may be used to produce an equivalent therapeutic or prophylactic effect. Generally, peptide mimetics are structurally similar to a paradigm polypeptide (i.e., a polypeptide that has a biochemical property or pharmacological activity), but have one or more peptide linkages optionally replaced by a chemical linkage not normally found in peptides by methods known in the art. Labeling of peptide mimetics usually involves covalent attachment of one or more labels, directly or through a spacer (e.g., an amide group), to non-interfering positions on the peptide mimetic that are predicted by quantitative structure-activity data and molecular modeling. Such non-interfering positions generally are positions that do not form direct contacts with the macromolecules to which the peptide mimetic binds to produce the therapeutic effect. Derivitization (e.g., labeling) of peptide mimetics should not substantially interfere with the desired biological or pharmacological activity of the peptide mimetic.

The use of peptide mimetics can be enhanced using combinatorial chemistry to create drug libraries. The design of peptide mimetics can be aided by identifying amino acid mutations that increase or decrease binding of a peptide to, for instance, a tumor cell. Approaches that can be used include the yeast two hybrid method (see Chien et al. (1991) Proc. Natl. Acad. Sci. USA 88, 9578-9582) and using the phage display method. The two-hybrid method detects protein-protein interactions in yeast (Fields et al. (1989) Nature 340, 245-246). The phage display method detects the interaction between an immobilized protein and a protein that is expressed on the surface of phages such as lambda and M13 (Amberg et al. (1993) Strategies 6, 2-4; Hogrefe et al. (1993) Gene 128, 119-126). These methods allow positive and negative selection for peptide-protein interactions and the identification of the sequences that determine these interactions.

Nucleic Acid Molecules

The present invention provides nucleic acid molecules that encode mTOR beta polypeptides.

As used herein, the terms "nucleic acid" and "polynucleotide" are used interchangeably and refer to a polymeric form of nucleotides of any length, either deoxyribonucleotides (adenine, guanine, thymine, and/or cytosine) or ribonucleotides, or analogs thereof. Such polynucleotides may be in a single stranded form, or in a double-stranded helix. This term refers only to the primary and secondary structure of the molecule and is not limited to any particular tertiary form. Non-limiting examples of polynucleotides include a gene, a gene fragment, DNA, messenger RNA (mRNA), cDNA, single-stranded RNA or DNA, double-stranded DNA found in linear DNA molecules (e.g., restriction fragments), viruses, chromosomes, recombinant polynucleotides, plasmids, vectors, isolated DNA of any sequence, isolated RNA of any sequence, nucleic acid probes, and primers. Polynucleotide sequences such as sequences of double-stranded DNA molecules, may be described herein according to the normal convention of giving only the sequence in the 5' to 3' direction along the non-transcribed strand of DNA (e.g., the strand having a sequence homologous to the mRNA).

A polynucleotide of the invention may be provided in isolated or purified form. As used herein, a nucleic acid molecule is said to be "isolated" when the nucleic acid molecule is substantially separated from contaminant nucleic acid molecules encoding other polypeptides.

A polynucleotide of the invention may be a polynucleotide (for example an RNA or DNA) that encodes a polypeptide of the invention as defined above. A polynucleotide of the invention may be a polynucleotide that is complementary to a nucleic acid sequence encoding a polypeptide of the invention. A polynucleotide of the invention may be a polynucleotide that hybridizes to a nucleic acid encoding a polypeptide of the invention across the open reading frame under appropriate stringency conditions. A polynucleotide of the invention may be a polynucleotide that encodes a polypeptide that shares at least about 75% or at least about 95% identity with the entire contiguous amino acid sequence of SEQ ID NO: 2.

Specifically contemplated are genomic DNA, cDNA, mRNA and antisense molecules, as well as nucleic acids based on alternative backbones or including alternative bases whether derived from natural sources or synthesized. Such nucleic acids, however, are defined further as being novel and unobvious over any prior art nucleic acid including that which encodes, hybridizes under appropriate stringency conditions, or is complementary to nucleic acid encoding a protein according to the present invention.

A polynucleotide of the invention may be any polynucleotide that encodes a polypeptide as described above. A polynucleotide of the invention may be any polynucleotide that encodes an mTORβ polypeptide. A polynucleotide of the invention may comprise a sequence that encodes the mTORβ polypeptide of SEQ ID NO: 2, a polypeptide comprising or consisting essentially of the mTORβ polypeptide of SEQ ID NO:2, or a variant or fragment of any thereof as described above. A polynucleotide of the invention may comprise, consist essentially or of consist of the nucleic acid sequence of SEQ ID NO: 1 or a nucleic acid sequence that varies from SEQ ID NO: 1 only through redundancy in the genetic code, i.e. another nucleic acid sequence that encodes the same polypeptide as SEQ ID NO: 1.

A nucleic acid "coding sequence" or a nucleic acid sequence which "encodes" a selected polypeptide is a nucleic acid molecule (e.g. DNA or RNA) which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A polyadenylation signal and transcription termination sequence will usually be located 3' to the coding sequence. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA.

A polynucleotide of the invention may be a naturally occurring nucleic acid that encodes an mTORβ polypeptide. For example, the polynucleotide of SEQ ID NO: 1 encodes the mTORβ polypeptide of SEQ ID NO: 2. A polynucleotide of the invention may be a variant of such a polypeptide or may encode a variant of a naturally occurring mTORβ polypeptide as described above.

A polynucleotide of the invention may encode a polypeptide having at least about 75% sequence identity, preferably at least about 80%, at least about 85%, at least about 90%, at least about 95% or more, at least about 97%, or most preferably at least about 99% or more identity with a naturally occurring mTORβ polypeptide, such as with the entire contiguous amino acid sequence of SEQ ID NO: 2. A polynucleotide of the invention may share at least 80%, preferably at least about 85%, at least about 90%, at least about 95% or more, at least about 97% or more, and most preferably 99% sequence identity with a naturally occurring mTORβ polynucleotide sequence, such as with the nucleotide sequence of SEQ ID NO: 1 or other polynucleotides encoding the polypeptide of SEQ ID NO: 2, particularly across the open reading frame.

Methods of measuring homology or identity are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified mTORβ polynucleotide or polypeptide sequence. For example the UWGCG Package provides the BESTFIT program which can be used to calculate homology (e.g. used on its default settings) (Devereux et al (1984) Nucleic Acids Research 12, p 387-395). The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Homology or sequence identity at the nucleotide or amino acid sequence level is preferably determined by BLAST (Basic Local Alignment Search Tool) analysis using the algorithm employed by the programs blastp, blastn, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference) which are tailored for sequence similarity searching. The approach used by the BLAST program is to first consider similar segments, with gaps (non-contiguous) and without gaps (contiguous), between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (1994) Nature Genetics 6, 119-129 which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992) Proc. Natl. Acad. Sci. USA 89, 10915-10919, fully incorporated by reference), recommended for query sequences over eighty-five nucleotides or amino acids in length.

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every wink$^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

A variant polynucleotide may differ from a sequence in the relevant polynucleotide by up to 3, up to 5, up to 10, up to 15, up to 20, up to 30, up to 50, up to 100 or more mutations (each of which may be a substitution, deletion or insertion). These mutations may be measured over a region of at least 30, for instance at least 40, 60 or 100 or more contiguous nucleotides of the variant, or across the full length of the variant or the polynucleotide from which it is derived.

A variant polynucleotide of the invention may hybridize with an mTORβ polynucleotide, such as a naturally occurring mTORβ polynucleotide, such as the polynucleotide of SEQ ID NO: 1, or the complement of any thereof, at a level significantly above background. The signal level generated by the interaction between the variant and the original polynucleotide is typically at least 10 fold, preferably at least 100 fold, as intense as "background hybridisation". The intensity of interaction may be measured, for example, by radiolabelling the probe, e.g. with $^{32}$P. Such a variant may or may not encode a polypeptide of the invention. Preferred molecules are those that hybridize to the complement of SEQ ID NO: 1 and which encode a functional protein, such as an mTORβ polypeptide as defined above. Even more preferred hybridizing molecules are those that hybridize under the above conditions to the complement strand of the open reading frame of SEQ ID NO: 1.

Such hybridization preferably occurs under stringent constitutions. "Stringent conditions" are those that (1) employ low ionic strength and high temperature for washing, for example, 0.015 M NaCl/0.0015 M sodium citrate/0.1% SDS at a temperature of at least 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer (pH 6.5) with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at a temperature of at least 42° C., with washes at 42° C. in 0.2×SSC and 0.1% SDS. A skilled artisan can readily determine and vary the stringency conditions appropriately to obtain a clear and detectable hybridization signal.

The present invention further provides fragments of the encoding nucleic acid molecule. A polynucleotide of the invention may thus be a fragment of any of the polynucleotides described herein or may encode a fragment polypeptide as described above. As used herein, a fragment of an encoding nucleic acid molecule refers to a small portion of the entire protein coding sequence. The size of the fragment will be determined by the intended use. For example, if the fragment is chosen to encode an active portion of the protein, the fragment will need to be large enough to encode the functional regions of the protein. If the fragment is to be used as a nucleic acid probe or PCR primer, then the fragment length is chosen to obtain a relatively small number of false positives during probing/priming.

Polynucleotide "fragments" according to the invention may be made by truncation, e.g. by removal of one or more nucleotides from one or both ends of a polynucleotide. Up to 10, up to 20, up to 30, up to 40, up to 50, up to 75, up to 100, up to 200 or more nucleic acids may be removed from the 3' and/or 5' end of the polynucleotide in this way. Fragments may also be generated by one or more internal deletions.

Fragments of the nucleic acid molecules of the present invention (i.e., synthetic oligonucleotides) may be used as probes or specific primers for the polymerase chain reaction (PCR), or to synthesize gene sequences encoding proteins of the invention. Such molecules can easily be synthesized by chemical techniques, for example, the phosphotriester method of Matteucci et al. (1981) J. Am. Chem. Soc. 103, 3185-3191 or using automated synthesis methods. In addition, larger DNA segments can readily be prepared by well-known methods, such as synthesis of a group of oligonucleotides that define various modular segments of the gene, followed by ligation of oligonucleotides to build the complete modified gene. In a preferred embodiment, a nucleic acid molecule of the present invention contains a contiguous open reading frame of at least about 2121 nucleotides.

A polypeptide of the invention may thus be produced from or delivered in the form of a polynucleotide which encodes, and is capable of expressing, it. Polynucleotides of the invention can be synthesised according to methods well known in the art, as described by way of example in Sambrook et al (1989, Molecular Cloning—a laboratory manual; Cold Spring Harbor Press). That is, polynucleotide sequences coding for the above-described polypeptides can be obtained using recombinant methods, such as by screening cDNA and genomic libraries, or by deriving the coding sequence for a polypeptide from a vector known to include the same. Furthermore, the desired sequences can be isolated directly from cells and tissues containing the same, using standard techniques, such as phenol extraction and PCR of cDNA or genomic DNA. Polynucleotide sequences can also be produced synthetically, rather than cloned.

The nucleic acid molecules of the present invention may further be modified to contain a detectable label for diagnostic and probe purposes. A variety of such labels is known in the art and can readily be employed with the encoding molecules herein described. Suitable labels include, but are not limited to, biotin, radiolabeled nucleotides, and the like. A skilled artisan can readily employ any such label to obtain labeled variants of the nucleic acid molecules of the invention. Modifications to the primary structure itself by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

Vectors and Host Cells

The polynucleotides of the invention may be provided in a vector, such as an expression vector. The polypeptides, polynucleotides and vectors of the invention may be provided in a host cell.

The present invention further provides recombinant DNA molecules (rDNA) that contain a coding sequence. As used herein, an rDNA molecule is a DNA molecule that has been subjected to molecular manipulation in situ. Methods for generating rDNA molecules are well known in the art, for example, see Sambrook et al. (2001), Molecular Cloning—A Laboratory Manual, Cold Spring Harbor Laboratory Press. In the preferred rDNA molecules, a coding DNA sequence is operably linked to expression control sequences and/or vector sequences. In one embodiment of the invention, the coding sequence contains SEQ ID NO: 1 or fragment thereof. In an alternate embodiment, the coding sequence encodes the polypeptide of SEQ ID NO: 2 or fragment thereof.

The nucleic acid molecules of the present invention may be provided in the form of an expression cassette which includes control sequences operably linked to the inserted sequence, thus allowing for expression of the polypeptide of the invention in vivo in a targeted subject species. These expression cassettes, in turn, are typically provided within vectors. A suitable vector may be any vector which is capable of carrying a sufficient amount of genetic information, and allowing expression of a polypeptide of the invention.

Vectors may be used to simplify manipulation of the nucleic acids of the invention, either for preparation of large quantities of nucleic acids for further processing (cloning vectors) or for expression of the polypeptides (expression vectors). Such proteins include mTORβ, proteins comprising one or more mutations at any amino acid residue of SEQ ID NO: 2 and derivative polypeptides, thereof. Vectors comprise plasmids, viruses (including phage), and integrated DNA fragments (i.e., fragments that are integrated into the host genome by recombination).

Once a coding sequence for an mTORβ polypeptide of the invention has been prepared or isolated, it can be cloned into any suitable vector and thereby maintained in a composition of cells, which is substantially free of cells that do not contain any mTORβ coding sequence. As described herein, numerous cloning vectors are known to those of skill in the art. Cloning vectors need not contain expression control sequences.

The present invention also includes expression vectors that comprise polynucleotide sequences or rDNA molecules of the invention. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al. Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably, also expression, of the polynucleotide of the invention e.g. of a structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 (BioRad), pPL and pKK223 (Pharmacia).

Expression vectors compatible with eukaryotic cells, preferably those compatible with vertebrate cells, can also be used to form vector or rDNA molecules that contain a coding sequence. Eukaryotic cell expression vectors, including viral vectors, are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC), the vector pCDM8 described herein, and the like eukaryotic expression vectors.

An exemplary eukaryotic expression system is that employing vaccinia virus, which is well-known in the art (see, for example, WO 86/07593). Yeast expression vectors are known in the art (see, for example, U.S. Pat. Nos. 4,446,235 and 4,430,428). Another expression system is vector pHSI, which transforms Chinese hamster ovary cells (see WO 87/02062). Mammalian tissue may be co-transformed with DNA encoding a selectable marker such as dihydrofolate reductase (DHFR) or thymidine kinase and DNA encoding mTORβ or derivative. If wild type DHFR gene is employed, it is preferable to select a host cell, which is deficient in DHFR, thus permitting the use of the DHFR coding sequence as marker for successful transfection in hgt medium, which lacks hypoxanthine, glycine, and thymidine.

Eukaryotic cell expression vectors used as vectors of the invention or used to construct the rDNA molecules of the present invention may further include a selectable marker that is effective in a eukaryotic cell, preferably a drug resistance selection marker. A preferred drug resistance marker is the gene whose expression results in neomycin resistance, i.e., the neomycin phosphotransferase (neo) gene. (Southern et al. (1982) J. Mol. Anal. Genet. 1, 327-341). Alternatively, the selectable marker can be present on a separate plasmid, and the two vectors are introduced by co-transfection of the host cell, and selected by culturing in the appropriate drug for the selectable marker.

Control sequences in an expression vector may include transcriptional and translational control sequences such as a transcriptional promoter, a sequence encoding suitable ribosome binding sites, and sequences, which control termination of transcription and translation. In one embodiment, the expression vector may include a selection gene to facilitate the stable expression of the mTORβ gene and/or to identify transformed cells. However, the selection gene for maintaining expression can be supplied by a separate vector in co-transformation systems using eukaryotic host cells.

Suitable vectors generally will contain a replicon (origins of replication, for use in non-integrative vectors) and control sequences, which are derived from species compatible with the intended expression host. By the term "replicable" vector as used herein, it is intended to encompass vectors containing such replicons as well as vectors, which are replicated by integration into the host genome Expression vectors for host cells ordinarily include an origin of replication, a promoter located upstream from the mTOR beta polypeptide coding sequence, together with a ribosome binding site, a polyadenylation site, and a transcriptional termination sequence. An expression vector may comprise transcriptional and translational control sequences.

These are DNA regulatory sequences, such as promoters, enhancers, polyadenylation signals, terminators, and the like, that provide for the expression of a coding sequence in a host cell. Those of ordinary skill will appreciate that certain of these sequences are not required for expression in certain hosts. An expression vector for use with microbes need only contain an origin of replication recognized by the host, a promoter that will function in the host, and a selection gene.

As used herein, a "promoter sequence" is a DNA regulatory region capable of binding RNA polymerase in a cell and initiating transcription of a downstream (3'direction) coding sequence. For purposes of defining the present invention, the promoter sequence is bounded (inclusively) at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes.

Commonly used promoters are derived from polyoma, bovine papilloma virus, CMV (cytomegalovirus, either murine or human), Rouse sarcoma virus, adenovirus, and simian virus 40 (SV40). Other control sequences (e.g., terminator, polyA, enhancer, or amplification sequences) can also be used.

An expression vector is constructed so that the mTORβ or derivative polypeptide coding sequence is located in the vector with the appropriate regulatory sequences. The positioning and orientation of the coding sequence with respect to the control sequences is such that the coding sequence is transcribed and translated under the "control" of the control sequences i.e., RNA polymerase which binds to the DNA molecule at the control sequences transcribes the coding sequence into mRNA. The control sequences may be ligated to the coding sequence prior to insertion into a vector, such as the cloning vectors previously described. Alternatively, the coding sequence can be cloned directly into an expression vector, which already contains the control sequences and an appropriate restriction site. If the selected host cell is a mammalian cell, the control sequences can be heterologous or homologous to the mTORβ or derivative polypeptide coding sequence and the coding sequence can be either genomic DNA containing introns or cDNA.

A "signal sequence" can be included before the coding sequence. This sequence encodes a signal peptide, N-terminal to the polypeptide that directs the polypeptide to the cell surface or instructs the host cell to secrete the polypeptide to the extracellular space. This signal peptide is clipped off by the host cell before the protein leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (see U.S. Pat. No. 4,546,082). Further, the alpha-factor and its analogs have been found to secrete heterologous proteins from a variety of yeast, such as *Saccharomyces* and *Kluyveromyces* (see e.g., EP 88312306.9, EP 0324274, and EP 0301669). An example for use in mammalian cells is the tPA signal used for expressing Factor VIIIc light chain.

A "heterologous" region of the nucleic acid construct is an identifiable segment of a nucleic acid within a larger nucleic acid molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns or synthetic sequences having codons different from the native gene).

The vectors and expression cassettes of the present invention may be administered directly as "a naked nucleic acid construct", preferably further comprising flanking sequences homologous to the host cell genome. As used herein, the term "naked DNA" refers to a vector such as a plasmid comprising a polynucleotide of the present invention together with a short promoter region to control its production. It is called "naked" DNA because the vectors are not carried in any delivery vehicle. When such a vector enters a host cell, such as a eukaryotic cell, the proteins it encodes are transcribed and translated within the cell.

The vector of the invention may thus be a plasmid vector, that is, an autonomously replicating, extrachromosomal circular or linear DNA molecule. Alternatively, the vectors of the present invention may be introduced into suitable host cells using a variety of viral techniques which are known in the art, such as for example infection with recombinant viral vectors such as retroviruses, herpes simplex viruses and adenoviruses. As an alternative to viral vectors, liposomal preparations can alternatively be used to deliver the nucleic acid molecules of the invention or the nucleic acid molecules of the present invention may be encapsulated, adsorbed to, or associated with, particulate carriers.

The present invention further provides cells that have been modified to express a polypeptide of the invention, such as host cells transformed with a nucleic acid molecule that encodes a polypeptide of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Such cells include transient, or preferably stable higher eukaryotic cell lines, such as mammalian cells or insect cells, and lower eukaryotic cells, such as yeast cells. Preferred eukaryotic host cells include, but are not limited to, yeast, insect and mammalian cells, preferably vertebrate cells such as those from a mouse, rat, monkey, or human cell line. Preferred eukaryotic host cells include Chinese hamster ovary (CHO) cells available from the ATCC as CCL61, NIH Swiss mouse embryo cells (NIH-3T3) available from the ATCC as CRL 1658, baby hamster kidney cells (BHK), and the like eukaryotic tissue culture cell lines. Preferably the cell line selected will be one which is not only stable, but also allows for mature glycosylation and cell surface expression of a polypeptide. Expression may be achieved in transformed oocytes. A suitable peptide may be expressed in cells of a transgenic non-human animal, preferably a mouse. A transgenic non-human animal expressing a peptide of the invention is included within the scope of the invention. A peptide of the invention may also be expressed in *Xenopus laevis* oocytes or melanophores.

Any prokaryotic host can be used to express a polynucleotide, vector or rDNA molecule encoding a polypeptide of the invention. In one embodiment, the preferred prokaryotic host is *E. coli*.

Transformation of appropriate cell hosts with a polynucleotide, vector or rDNA molecule of the present invention is accomplished by well-known methods that typically depend on the type of vector used and host system employed. With regard to transformation of prokaryotic host cells, electroporation and salt treatment methods are typically employed, see, for example, Cohen et al. (1972) Proc. Natl. Acad. Sci. USA 69, 2110; and Sambrook et al. (1989) Molecular Cloning—A Laboratory Manual, Cold Spring Harbor Laboratory Press. With regard to transformation of vertebrate cells with vectors containing rDNAs, electroporation, cationic lipid, or salt treatment methods are typically employed, see, for example, Graham et al. (1973) Virol. 52, 456; Wigler et al. (1979) Proc. Natl. Acad. Sci. USA 76, 1373-1376.

Successfully transformed cells, i.e., cells that contain a polynucleotide, vector or rDNA molecule of the present invention, can be identified by well-known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern ((1975) J. Mol. Biol. 98, 503-504) or Berent et al. ((1985) Biotech. 3, 208-209) or the proteins produced from the cell assayed via an immunological method.

Such cell lines of the invention may be cultured using routine methods to produce a polypeptide of the invention, or may be used therapeutically or prophylactically to deliver polypeptides of the invention to a subject. For example, cell lines capable of secreting a polypeptide of the invention may be administered to a subject. Alternatively, polynucleotides, expression cassettes or vectors of the invention may be administered to a cell from a subject ex vivo and the cell then returned to the body of the subject. For example, methods for the ex vivo delivery and reimplantation of transformed cells into a subject are known (e.g., dextran-mediated transfection, calcium phosphate precipitation, electroporation, and direct microinjection into nuclei).

Depending on the expression system and host selected, the peptide of interest, such as mTORβ or a variant or derivative thereof, may be produced by growing host cells transformed by an exogenous or heterologous DNA construct, such as an expression vector described above under conditions whereby the polypeptide is expressed. The peptide of interest, such as mTORβ or derivative polypeptides thereof, is then isolated from the host cells and purified. If the expression system secretes the protein or peptide into the growth media, the protein can be purified directly from cell-free media. The selection of the appropriate growth conditions and initial crude recovery methods are within the skill of the art.

Transformed host cells are cells which have been transformed or transfected either with vectors containing mTORβ or mTORβ derivative polypeptide encoding nucleic acid. The expressed polypeptides may be secreted into the culture supernatant, under the control of suitable processing signals in the expressed peptide (e.g., homologous or heterologous signal sequences).

A cell has been "transformed" by an exogenous or heterologous nucleic acid when such nucleic acid as been introduced inside the cell. The transforming nucleic acid may or may not be integrated (covalently linked) into chromosomal DNA making up the genome of the cell. In prokaryotes, for example, the transforming nucleic acid may be maintained on an episomal element such as a plasmid or viral vector. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming nucleic acid.

As used herein, a "cell line" is a clone of a primary cell that is capable of stable growth in vitro for many generations. As used herein, nucleic acid sequences display "substantial identity" when at least about 85 percent (preferably at least about 90 percent, more preferably at least about 95, more preferably at least about 97 and most preferably at least about 99 percent) of the nucleotides match over the defined length of the nucleotide sequences. Sequences that are substantially identical can be identified in a Southern hybridization experiment under, for example, stringent conditions as defined for that particular system. Defining appropriate hybridization conditions is within the skill of the art.

Higher eukaryotic cell cultures may be used to express the proteins of the present invention, whether from vertebrate or invertebrate cells, including insects, and the procedures of propagation thereof are known.

Production of Recombinant Proteins Using an rDNA Molecule

The present invention further provides methods for producing a protein of the invention using nucleic acid molecules herein described. In general terms, the production of a recombinant form of a protein typically involves the following steps. First, a nucleic acid molecule is obtained that encodes a protein of the invention, such as a nucleic acid molecule comprising, consisting essentially of, or consisting of the nucleic acid sequence encoding an amino acid of SEQ ID NO: 2 or derivatives thereof. Second, the nucleic acid molecule is then preferably placed in operable linkage with suitable control sequences, as described above, to form an expression unit containing the protein open reading frame.

The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence to provide an excisable gene to insert into these vectors. A skilled artisan can readily adapt any host/expression system known in the art for use with the nucleic acid molecules of the invention to produce recombinant protein.

Antibodies

Another class of agents of the present invention are antibodies immunoreactive with mTOR beta (mTORβ). In a preferred embodiment, the antibodies are immunoreactive with mTOR beta (mTORβ) but not with mTOR alpha. Antibody agents are obtained by immunization of suitable mammalian subjects with peptides, containing as antigenic regions, those portions of the protein intended to be targeted by the antibodies. The antibodies may be polyclonal or monoclonal.

Antibodies which bind to the active sites of mTOR beta are encompassed in the invention. In one embodiment of the invention, the antibody binds to the active site of mTOR beta that phosphorylates 4E-BP1. In another embodiment of the invention, the antibody binds to the active site of mTOR beta that phosphorylates S6K1. In an alternate embodiment, the antibody binds to the site in mTOR beta that leads to the induction of cMyc expression.

Antibodies capable of inhibiting the activity of this protein are also encompassed in the invention.

Antibodies are prepared by immunizing suitable mammalian hosts in appropriate immunization protocols using the peptides, polypeptides, or proteins of the invention, such as mTOR beta (mTORβ), variants and isolated binding partners, if they are of sufficient length, or, if desired, or if required to enhance immunogenicity, conjugated to suitable carriers. Methods for preparing immunogenic conjugates with carriers such as bovine serum albumin (BSA), keyhole limpet hemocyanin (KLH), or other carrier proteins are well known in the art. In some circumstances, direct conjugation using, for example, carbodiimide reagents may be effective; in other instances linking reagents well known in the art, may be desirable to provide accessibility to the hapten. The hapten peptides can be extended at either the amino or the carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

Anti-peptide antibodies can be generated using synthetic peptides corresponding to, for example, the carboxy terminal 15 amino acids of mTOR beta (mTORβ). Antibodies which bind to the phosphorylation site on a kinase can also be generated and include antibodies which bind to the phosphorylation site on the mTOR beta (mTORβ) protein. Synthetic peptides can be as small as 1 to 3 amino acids in length, but are preferably at least 4 or more amino acid residues long. The peptides are coupled to KLH using standard methods and can be immunized into animals such as rabbits. Polyclonal anti-mTOR beta (mTORβ) antibodies can then be purified, for example by using Actigel beads containing the covalently bound peptide.

While the polyclonal antisera produced in this way may be satisfactory for some applications, for pharmaceutical compositions, use of monoclonal preparations is preferred. Immortalized cell lines, which secrete the desired monoclonal antibodies, may be prepared using the standard method of Kohler and Milstein or modifications, which effect immortalization of lymphocytes or spleen cells, as is generally known. The immortalized cell lines secreting the desired antibodies are screened by immunoassay in which the antigen is the peptide hapten. polypeptide or protein. When the appropriate immortalized cell culture secreting the desired antibody is identified, the cells can be cultured either in vitro or by production in ascites fluid. Of particular interest, are monoclonal antibodies that recognize the FK506/Rapamycin domain, the kinase domain, or the regulatory domain.

The desired monoclonal antibodies are then recovered from the culture supernatant or from the ascites supernatant. Fragments of the monoclonals or the polyclonal antisera that contain the immunologically significant portion can be used as antagonists, as well as the intact antibodies. Use of immunologically reactive fragments, such as Fav, $_{sc}$FV, Fab, Fab' or F(ab')$_2$ fragments is often preferable, especially in a therapeutic context, as these fragments are generally less immunogenic than the whole immunoglobulin.

Antigen binding fragments such as F(ab)2, Fab and Fv fragments may be used, i.e. antibody fragments from the "variable" regions of an antibody that comprise the antigen binding site. Antibodies may be human, humanized, or chimeric variants of the foregoing. Such antibodies can be less immunogenic when administered to a subject. Methods of producing humanized or chimeric antibodies are well known in the art. The antibodies contemplated also include different isotypes and isotype subclasses (e.g., IgG$_1$, IgG$_2$, and IgM). These antibodies can be prepared by raising them in vertebrates, in hybridoma cell lines or other cell lines, or by recombinant means. For references on how to prepare these antibodies, see Harlow & Lane (1988), Antibodies: A Laboratory Manual, Cold Spring Harbor Press.

The antibodies or fragments may also be produced, using current technology, by recombinant means. Regions that bind specifically to the desired regions of receptor can also be produced in the context of chimeras with multiple species origin.

Methods of Treatment

This invention also relates to methods for the treatment of a disease associated with aberrant expression of mTOR beta, comprising administration of an effective amount of an agent, to a subject in need thereof, capable of modulating the activity and/or expression of mTOR beta. Such an agent may therefore be used in the treatment (which may be therapeutic and/or prophylactic), diagnosis or prevention of such a disease. The aberrant expression may be, for example, increased expression of mTOR beta or decreased expression of mTOR beta. A suitable agent may be selected depending upon whether the level of mTOR beta is to be supplemented or reduced.

In one embodiment, the agent is an inhibitor of mTOR beta. Such an inhibitor may act to reduce the amount of mTOR beta that is present, for example by inhibitor or preventing mTOR beta gene expression or protein production or by acting to remove or break down mTOR beta mRNA or protein. Such an inhibitor may act to reduce the activity of mTOR beta, for example any activity or function of mTOR beta as discussed above. A suitable inhibitor may be a molecule that binds to mTOR beta and prevents its function. For example, a suitable inhibitor may be an antibody that binds to mTOR beta. In another embodiment, the agent is an mTOR beta antagonist.

In another embodiment, the agent is a promoter or activator of mTOR beta. Such an agent may act to increase the amount of mTOR beta protein that is present. For example, the agent may be a polynucleotide, vector, rDNA, polypeptide or host cell as described herein. The agent may act to increase the life span of an mTOR beta mRNA or polypeptide, for example by increasing the resistance of the mRNA or polypeptide to degradation processes within the cell or organism. Such an agent may act to increase the activity or function of mTOR beta, for example any activity or function of mTOR beta as discussed above.

An effective amount of capable of modulating the activity and/or expression of mTOR beta may be an amount which exerts a suitable effect as described herein. For example, a suitable amount of an mTOR beta inhibitor may be that which is sufficient to exert an inhibitory effect on the activity of mTOR beta. An effective amount may also be an amount that is effective to inhibit the proliferation of cells exhibiting aberrant mTOR beta expression.

In some embodiments of this method, the disease associated with aberrant expression of mTOR beta is cancer, including, but not limited to, prostate cancer, breast cancer, multiple myeloma, lung cancer, non-small cell lung carcinoma, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, lymphocytic lymphomas, cancer of the bladder, cancer of the kidney or ureter, renal cell carcinoma, carcinoma of the renal pelvis, neoplasms of the central nervous system (CNS), neuroectodermal cancer, spinal axis tumors, glioma, meningioma, pituitary adenoma, or a combination of one or more of the foregoing cancers. In another embodiment of said method, said abnormal cell growth is a benign proliferative disease, including, but not limited to, psoriasis, benign prostatic hyperplasia, hypertrophy, or restinosis.

In one embodiment of the invention, the agent is a kinase inhibitor. Exemplary types of kinase inhibitors which can be used in the methods of the invention include, but are not limited to, rapamycin, rapamycin derivatives such as e.g. RAD001 (Lane (2003) Mol. Targets. Cancer Therapeut. 259-260), CCI-779 and AP23573.

In practicing the methods of this invention, these agents may be used alone or in combination with other active or inactive ingredients. The methods of the invention therefore include administration of a polypeptide comprising these agents linked to a cytotoxic agent for the treatment of a disease associated with abnormal cell growth, including cancer. Examples of cytotoxic agents include, but are not limited to, gelonin, ricin, saponin, *pseudonomas* exotoxin, pokeweed antiviral protein, diphtheria toxin, complement proteins, or any other agent known in the art that is capable of killing a cell upon contact with that cell.

The present invention also extends to compositions, such as pharmaceutical compositions comprising molecules and agents as described herein. Formulation of a composition comprising a molecule of the invention, such as a polynucleotide, expression cassette, vector, polypeptide, cell or antibody as described above, can be carried out using standard pharmaceutical formulation chemistries and methodologies all of which are readily available to the reasonably skilled artisan. For example, compositions containing one or more molecules of the invention can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

The present invention thus further provides compositions comprising a molecule as described herein such as a polypeptide of the invention, e.g., mTOR beta or a variant or derivative thereof, and a diluent. Suitable diluents can be aqueous or non-aqueous solvents or a combination thereof, and can comprise additional components, for example water-soluble salts or glycerol, that contribute to the stability, solubility, activity, and/or storage of the protein or polypeptide.

The pharmaceutical composition may also comprise, consist of, or consist essentially of one or more agents capable of modulating the activity and/or expression of mTOR beta and a pharmaceutically acceptable carrier. Such a composition may comprise an agent to be administered as part of a therapeutic method of the invention as described above. The pharmaceutical compositions of the present invention may contain suitable pharmaceutically acceptable carriers comprising excipients and auxiliaries that facilitate processing of the active compounds into preparations that can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate, or triglycerides. Aqueous injection suspensions may contain substances which increase the viscosity of the suspension. Examples of such viscosity increasing substances include are sodium carboxymethyl cellulose, sorbitol and dextran. Optionally, the suspension may also contain stabilizers. Liposomes can also be used to encapsulate the agent for delivery into the cell.

Pharmaceutical compositions of the invention, such as those comprising one or more agents capable modulating the activity and/or expression of mTOR beta, can be administered via parenteral, subcutaneous, intravenous, intramuscular, intraperitoneal, intrathecal, intracranial or transdermal or buccal routes. For example, an agent may be administered locally to a tumor or the site of aberrant mTOR beta expression via microinfusion. Alternatively, or concurrently, administration may be by the oral route. The dosage administered will be dependent upon the age, health, and weight of the recipient, kind of concurrent treatment, if any, frequency of treatment, and the nature of the effect desired.

While individual needs vary, determination of optimal ranges of effective amounts of each component is within the skill of the art. Dosages of an agent capable of modulating the activity and/or expression of mTOR beta of the present invention typically comprise about 1.0 ng/kg body weight to about 0.13 mg/kg body weight. In one embodiment, dosages of an agent capable of modulating the activity and/or expression of mTOR beta comprise about 1.0 ng/kg body weight to about 0.1 mg/kg body weight. In a preferred embodiment, dosages for systemic administration comprise about 0.01 µg/kg body weight to about 0.1 mg/kg body weight. In another embodiment, the dosage of an agent capable of modulating the activity and/or expression of mTOR beta comprises less than about 0.1 mg/kg body weight. More preferred dosages for systemic administration comprise about 0.1 µg/kg body weight to about 0.05 mg/kg body weight. In another preferred embodiment, the dosage of an agent capable of modulating the activity and/or expression of mTOR beta comprises less than about 0.05 mg/kg body weight. The most preferred dosages for systemic administration comprise between about 1.0 µg/kg body weight to about 0.01 mg/kg body weight. In other embodiments, the amount of an agent capable of modulating the activity and/or expression of mTOR beta administered is an amount effective to bring the concentration of an agent capable of modulating the activity and/or expression of mTOR beta in the serum to a concentration of about 20.0, 10.0, 5.0, 2.50, 1.25, 0.625, 0.3125, 0.156, 0.078, 0.039, 0.020, 0.010, 0.005, 0.003, 0.0015, 0.0008, 0.0003, or 0.0001 nM. The preferred dosages for direct administration to a site via micro-infusion comprise 1 ng/kg body weight to 1 mg/kg body weight.

The pharmaceutical formulation for systemic administration according to the invention may be formulated for enteral, parenteral, or topical administration. Indeed, all three types of formulations may be used simultaneously to achieve systemic administration of the active ingredient.

As mentioned above for some methods of the invention, topical administration may be used. Any common topical formulation such as a solution, suspension, gel, ointment or salve and the like may be employed. Preparation of such topical formulations are described in the art of pharmaceutical formulations as exemplified, for example, by Gennaro et al. (2000) Remington's Pharmaceutical Sciences, Mack Publishing. For topical application, the compositions could also be administered as a powder or spray, particularly in aerosol form. In some embodiments, the compositions of this invention may be administered by inhalation. For inhalation therapy, the active ingredients may be in a solution useful for administration by metered dose inhalers or in a form suitable for a dry powder inhaler. In another embodiment, the compositions are suitable for administration by bronchial lavage.

Suitable formulations for oral administration include hard or soft gelatin capsules, pills, tablets, including coated tablets, elixirs, suspensions, syrups or inhalations and controlled release forms thereof.

The compositions and methods of the invention for therapeutic purposes can be utilized in vivo, ordinarily in mammals, such as e.g., humans, sheep, horses, cattle, pigs, dogs, cats, rats, and mice or ex vivo. The invention is particularly useful in the treatment of human subjects.

Methods to Identify Agents that Modulate Expression and/or Activity of mTOR Beta The present invention also provides for methods identifying (i.e., screening) for an agent that modulates mTOR beta expression and/or activity. In one embodiment of the invention, the agent modulates mTOR beta expression. In another embodiment, the agent modulates mTOR beta activity. A decrease of mTOR expression and/or activity is indicative of an agent that inhibits mTOR beta. An increase of mTOR expression and/or activity is indicative of an agent that stimulates mTOR beta.

Another embodiment of the present invention provides methods for identifying agents that modulate the expression of a nucleic acid encoding a mTOR beta (mTORβ) protein, such as a protein having the amino acid sequence of SEQ ID NO: 2. Such assays may utilize any available means of monitoring for changes in the expression level of the nucleic acids of the invention. As used herein, an agent is said to modulate the expression of a nucleic acid of the invention, for instance a nucleic acid encoding the protein having the sequence of SEQ ID NO: 2 or a nucleic acid having SEQ ID NO: 1, if it is capable of up- or down-regulating expression of the nucleic acid in a cell.

The invention thus provides methods for the screening or identification of agents that modulate the activity and/or expression of mTOR beta.

A method of the invention may comprise the following steps:
(a) providing a polypeptide of the invention (such as a polypeptide of the invention or a polypeptide encoded by a polynucleotide of the invention);
(b) contacting said polypeptide with a test agent; and
(c) detecting any change in the activity of said polypeptide, wherein a change in activity is indicative of an agent capable of modulating mTOR beta activity.

Equivalent methods may also be carried out using a polynucleotide of the invention, for example to identify an agent capable of modulating gene expression, or an agent capable of modulating the level of, or transcriptions of, mTOR beta mRNA.

A method of the invention may be carried out in vitro or in vivo. A method of the invention may be carried out using an isolated (or substantially isolated) or purified (or substantially purified) polypeptide.

Alternatively a method may be carried out in a cell that comprises the polypeptide. For example, such a method may comprise the following steps:
(a) providing a host cell of the invention, such as a host cell that comprises or expresses a polypeptide of the invention (such as a polypeptide of the invention or a polypeptide encoded by a polynucleotide of the invention);
(b) contacting said host cell with a test agent; and
(c) detecting any change in the expression and/or activity of said polypeptide, wherein a change in expression and/or activity is indicative of an agent capable of modulating mTOR beta expression and/or activity.

A particular method may comprise the following steps:
(a) exposing a cell expressing a polypeptide of the invention to the agent; and
(b) detecting the change in expression and/or activity of said polypeptide, wherein a change in expression and/or activity is indicative of an agent capable of modulating mTOR beta expression and/or activity.

In one assay format, cell lines that contain reporter gene fusions between the open reading frame of the mTOR beta (e.g. SEQ ID NO: 1) and any assayable fusion partner may be prepared. Numerous assayable fusion partners are known and readily available including the firefly luciferase gene and the gene encoding chloramphenicol acetyltransferase (Alam et al., 1990 Anal. Biochem. 188, 245-254). Cell lines containing the reporter gene fusions are then exposed to the agent or a control to be tested under appropriate conditions and time. Differential expression of the reporter gene between samples exposed to the agent and control samples identifies agents, which modulate the expression of a nucleic acid encoding the mTOR beta.

In another assay format, the ability of an agent to modulate mTOR beta expression is based on measuring the expression of proteins such as e.g., c-Myc whose expression is modulated as a result of modulation of mTOR beta expression.

Additional assay formats may be used to monitor the ability of the agent to modulate the expression of a nucleic acid encoding a protein of the invention such as mTOR beta. For instance, mRNA expression may be monitored directly by hybridization to the nucleic acids of the invention. Cell lines are exposed to the agent and/or a polypeptide comprising a mTOR beta to be tested under appropriate conditions and time and total RNA or mRNA is isolated by standard procedures such those disclosed in Sambrook et al. (2001) Molecular Cloning, A Laboratory Manual, Cold Spring Harbor Laboratory Press.

Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al. (2001) or Ausubel et al. (1995) Current Protocols in Molecular Biology, Greene Publishing Company).

Hybridization conditions are modified using known methods, such as those described by Sambrook et al. (2001) and Ausubel et al. (1995) as required for each probe. Hybridization of total cellular RNA or RNA enriched for polyA RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a porous glass wafer. The glass wafer can then be exposed to total cellular RNA or polyA RNA from a sample under conditions in which the affixed sequences will specifically hybridize. Such glass wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding the mTOR beta protein.

The present invention also provides methods for identifying agents that modulate at least one activity of an mTOR beta polypeptide such as the polypeptide of SEQ ID NO: 2. Such methods or assays may utilize any means of monitoring or detecting the desired activity. These assays may include detection of phosphorylation of mTOR beta, detection of phosphorylation of S6K1, detection of phosphorylation of 4E-BP1, monitoring induction of cMyc expression or monitoring for the ability of S6K1 and/or 4E-BP1 to phosphorylate a second protein. In one embodiment of the invention, the activity of mTOR beta is detected based on detecting phosphorylation of PKB/Akt.

In one format, the specific activity of a protein of the invention, normalized to a standard unit, between a cell population that has been exposed to the agent to be tested compared to an un-exposed control cell population may be assayed. Cell lines or populations are exposed to the agent to be tested under appropriate conditions and time. Cellular lysates may be prepared from the exposed cell line or population and a control, unexposed cell line or population. The cellular lysates are then analyzed with the probe.

Antibody probes can be prepared by immunizing suitable mammalian hosts utilizing appropriate immunization protocols using the proteins of the invention or antigen-containing fragments thereof. To enhance immunogenicity, these proteins or fragments can be conjugated to suitable carriers. Methods for preparing immunogenic conjugates with carriers such as BSA, KLH or other carrier proteins are well known in the art. In some circumstances, direct conjugation using, for example, carbodiimide reagents may be effective; in other instances, linking reagents such as those supplied by Pierce Chemical Co. may be desirable to provide accessibility to the hapten. The hapten peptides can be extended at either the amino or the carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using standard methods, see e.g., Kohler & Milstein (1992) Biotechnology 24, 524-526 or modifications which effect immortalization of lymphocytes or spleen cells, as is generally known. The immortalized cell lines secreting the desired antibodies can be screened by immunoassay in which the antigen is the peptide hapten, polypeptide, or protein. When the appropriate immortalized cell culture secreting the desired antibody is identified, the cells can be cultured either in vitro or by production in ascites fluid.

The desired monoclonal antibodies may be recovered from the culture supernatant or from the ascites supernatant. Fragments of the monoclonal antibodies or the polyclonal antisera that contain the immunologically significant portion can be used as antagonists, as well as the intact antibodies. Use of immunologically reactive fragments, such as Fab or Fab' fragments, is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin. Antibody regions that bind specifically to the desired regions of the protein can also be produced in the context of chimeras with multiple species origin, for instance, humanized antibodies. The antibody can therefore be a humanized antibody or human antibody, as described in U.S. Pat. No. 5,585,089 or Riechmann et al. (1988) Nature 332, 323-327.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a non-random basis which takes into account the sequence of the target site or its conformation in connection with the agent's action. Agents can be rationally selected or rationally designed by utilizing the peptide sequences that make up these sites. For example, a rationally selected peptide agent can be a peptide whose amino acid sequence is identical to or a derivative of any functional consensus site.

The agents of the present invention can be, as examples, peptides, peptide mimetics, antibodies, antibody fragments, small molecules, vitamin derivatives, as well as carbohydrates. Peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Methods to Identify Binding Partners

Another embodiment of the present invention provides methods for use in isolating and identifying binding partners of mTOR beta or derivative. In general, a protein of the invention is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner, which bound to the protein of the invention, can then be removed and further analyzed. To identify and isolate a binding partner, the entire protein, for instance a protein comprising the entire amino acid sequence of SEQ ID NO: 2 or a protein encoded by a nucleotide of SEQ ID NO: 1, can be used. Alternatively, a fragment of the protein can be used.

As used herein, a cellular extract refers to a preparation or fraction that is made from a lysed or disrupted cell. The preferred source of cellular extracts will be cells derived from human skin tissue or the human respiratory tract or cells derived from a biopsy sample of human lung tissue in patients with allergic hypersensitivity. Alternatively, cellular extracts may be prepared from normal tissue or available cell lines, particularly granulocytic cell lines.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture. To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide/binding partner pairs from other constituents found in the extract. The identified binding partners can be either a single protein or a complex made up of two or more proteins. Alternatively, binding partners may be identified using a Far-Western assay according to the procedures of Takayama et al. (1997) Methods Mol. Biol. 69, 171-184 or Sauder et al. (1996) J. Gen. Virol. 77, 991-996 or identified using epitope tagged proteins or GST fusion proteins.

Alternatively, the nucleic acid molecules of the invention can be used in a yeast two-hybrid system. The yeast two-hybrid system has been used to identify other protein partner pairs and can readily be adapted to employ the nucleic acid molecules herein described.

Without further description, it is believed that one of ordinary skill in the art can, using the preceding description and the following illustrative examples, make and utilize the agents of the present invention (e.g., nucleic acids and polypeptides) and practice the claimed methods. The following working examples describe embodiments of the present invention, and are not to be construed as limiting in any way the remainder of the disclosure.

EXAMPLES

Example 1

Western Blot Analysis of Rat Tissues with the C-Terminal of mTOR Antibody

In contrast to yeasts, which have two TOR genes, mammals possess only one gene, known to encode a single polypeptide with molecular weight of approximately 280 kDa. To further elucidate the regulation and downstream signaling of mTOR, a monoclonal antibody (F11) was developed. This antibody (F11) recognizes specifically mTOR in Western blotting, immunoprecipitation and immunofluorescence (data not shown). The fragment of mTOR (350 amino acids in length), corresponding to the HEAT domains, was expressed in bacteria as a GST-fusion protein and used for immunization and screening for specific hybridoma clones. When this generated antibody was used to analyze in Western blotting the total cell lysates from rat tissues and various cell lines, predominantly one immunoreactive band of approximately 280 kDa was observed (see FIG. 1, lower panel). However, when a commercially available mTOR antibody (Cell Signalling) generated against the C-terminal peptide was used, several strong immunoreactive bands were detected (FIG. 1, upper panel). In addition to a 280-kDa band, which is highly abundant in rat brain, there were two strong immunoreactive bands of approximately 80 kDa and 95 kDa. The 80-kDa band is highly expressed in liver, blood, kidney, small, and large intestine, while lung, stomach, spleen, testis, and fat have medium/low level of expression. Interestingly, the 95-kDa band seems to be organ specific as it is only detected at a very high level in liver (see FIG. 1, upper panel). Furthermore, liver and blood possess a relatively weak but distinctive band of approximately 135 kDa. Re-probing of the membrane with anti-actin antibody served as a protein loading control. The detection of mTOR immunoreactive bands with lower molecular weights could be explained by the existence of mTOR splicing forms or by proteolytic degradation of a full-length protein.

Experimental Procedures for Plasmid Construction, siRNA and Expression Studies

For expression in mammalian cells, the full-length cDNA for mTORβ was cloned into the tagged eukaryotic expression vector pcDNA3.1/FLAG (Invitrogen). Kinase inactive point mutant of mTORβ with the substitution of Asp 514 to Glu (analog of Asp 2357 to Glu in TORα) was generated with the use of a site-directed mutagenesis kit (Stratagene) according to manufacturer's recommendations. Transient transfections of cells were carried out with the use of ExGene 500 reagent (Fermentas), under conditions recommended by the manufacturer. The mTOR siRNA was obtained from MWG Biotech (21 nucleotide in length, corresponding to the 2241-2261 region of human mTOR (Kim et al. 2002)). siRNA was transfected into Hek293 cells using Lipofectamine 2000 (Invitrogen) as recommended by manufacturer. The C-terminal region of S6K1 (His-S6K1C, amino acids 332-502) was cloned into pET24a plasmid (Novagene) in-frame with the 6His-tag sequence. The expression and affinity purification of His-S6K1C was carried out in BL21 DE3 cells using NTA-agarose (Qiagene), respectively. pCMV FLAG mTORα plasmid was kindly provided by Prof. K. Yonezawa, Kobe, Japan.
Reagents, Antibodies, and Cell Cultures Anti-FLAG tag, anti-HA tag and anti-β actin antibodies were purchased from Sigma. The N-terminal anti-mTOR antibody was from SantaCruz. All other antibodies were purchased from Cell Signaling. Human embryonic kidney HEK293 cells, human breast MCF7 and Human liver HepG2 cells were maintained at 37° C. and 5% $CO_2$ in Dulbecco's modified Eagle's medium supplemented with 10% fetal bovine serum (FBS; Hyclone), 2 mM L-glutamine, 50 units/ml penicillin, and 50 μg/ml streptomycin.
Experimental Procedures for RNA Purification and RT-PCR Total RNA was purified from HEK293, MCF7 and HepG2 cell lines using SV Total RNA Isolation System (Promega). The first strand cDNA was synthesized by annealing 10 μg of total RNA and 5 μg of oligo dT primer using ReverAid H Minus First Strand cDNA Synthesis Kit (Fermentas) at 70° C. for 5 minutes. Then RT mix (final 1× reaction buffer, 40 U RiboLock ribonuclease inhibitor (Fermentas), and 1 mM dNTP) was added and the solution and incubated for 5 minutes at 25° C. After the addition of RevertAid H Minus Reverse Transcriptase (Fermentas), the 25-μl reaction mix was incubated for 10 minutes at 25° C. and 1 hour at 37° C. The reverse transcriptase reaction was stopped by incubating for 10 minutes at 70° C. The reaction mixture was stored at −20° C. and 1 μl was used for each PCRs. The RT-PCR was performed using a panel of specific primers for mTOR. Specific fragments of glyceraldehyde-3-phosphate dehydrogenase (GADPH) and β-actin were amplified and used as loading and quality controls of first strand DNA.

Example 2

Northern Blot Analysis of mTOR in Human Tissue

Figure 2:
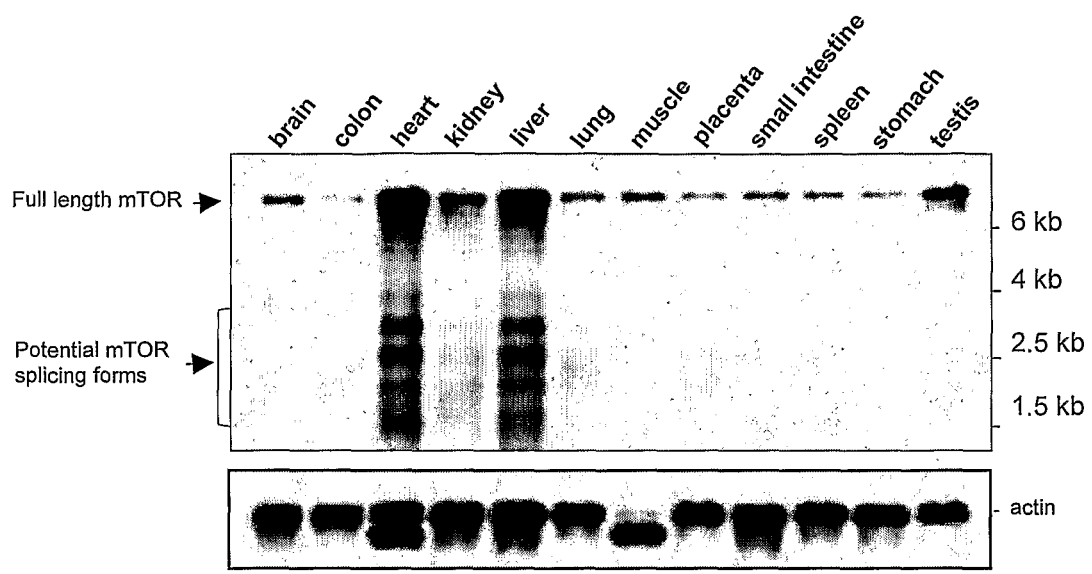
FIG. 2 shows a Northern blot analysis of mTOR expression in human tissues. The blot was stripped and reprobed for β-actin expression (lower panel).

To investigate these possibilities, i.e., the existence of mTOR splicing forms or proteolytic degradation of the full-length protein, a Northern blot analysis of total RNA samples purified from a panel of human tissues (OriGene) was initially performed. The membrane was probed with a DIG-labelled mTOR probe (750 bp), corresponding to its C-terminal coding region. In this analysis, the presence of several bands, which hybridized specifically with the mTOR probe (FIG. 2) were observed. As expected, ubiquitously expressed band of approximately 8.6 Kb, which would correspond to the full-length mTOR transcript, were also observed. In addition, there were several distinct bands in the region of 1.5 to 3.5 Kb that showed high abundance in liver and heart. The strongest signal corresponded to bands of 2.7 Kb and 3.2 Kb. The results obtained in Western and Northern blot analysis strongly implied the existence of mTOR splicing forms. The Northern blot analysis also indicates that mTORβ is highly expressed in heart and liver, while kidney, liver, blood, small and large intestine have the highest protein level of mTORβ.
Experimental Procedures for Northern Blot Analysis The membrane-containing poly(A)+ RNA samples from various human tissues was purchased from OriGene. The Northern blot analysis was performed using DIG Northern Starter kit (Roche Diagnostics) as recommended by the manufacturer. The mTOR DIG-labeled RNA probe was generated by using a 750 bp PCR product, corresponding to the C-terminal coding region of mTOR, as a template for the in vitro transcription reaction with dioxigenin-11-UTP. The actin probe was supplied by the manufacturer.

Example 3

Immunoprecipitation of mTOR Beta

Figure 3:
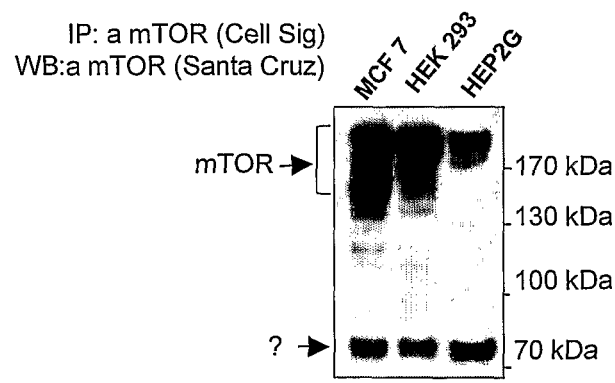
FIG. 3 shows immunoprecipitation of mTORβ from Hep2G, Hek293 and MCF7 cells with the C-terminal anti-mTOR antibodies. The lysates of Hep2G, Hek293 and MCF7 cells were immunoprecipitated with the C-terminal anti-mTOR antibodies' (Cell Signaling) and immune complexes probed in Western blotting with the N-terminal anti-mTOR antibodies
(Santa Cruz).

To further examine the nature of observed immunoreactive bands, mTOR was immunoprecipitated from Hek293, MCF7, and Hep2G cells using the C-terminal polyclonal antibody (Cell Signalling) and probed immune complexes in Western blotting with the N-terminal mTOR antibody. As shown in FIG. 3, two immunoreactive bands in the range of 280 kDa and 80 kDa were clearly detected in the immunoprecipitates from all three cell lines. However, mTOR was immunoprecipitated mTOR from these cell lines by using F11 Mabs, only one immunoreactive band of 280 kDa was observed (data not shown). The obtained results strongly suggest the existence of a potential mTOR splice form which would possess both the N- and C-terminal sequences and code a protein of approximately 700 amino acids in length. Therefore, the most abundant transcripts of 2.7 Kb and 3.2 Kb, which were detected in mTOR Northern blotting, have the potential to encode a splice variant of 80 kDa.
Experimental Procedures for Immunoprecipitation HEK293 cells were washed with ice-cold phosphate-buffered saline (PBS) and extracted with the lysis buffer containing 50 mM HEPES (pH 7.5), 150 mM NaCl, 1% (v/v) Triton X100, 2 mM EDTA, 50 mM sodium fluoride, 10 mM sodium pyrophosphate, 1 mM sodium orthovanadate, and a mixture of protease inhibitors (Roche Applied Science). Whole-cell extracts were centrifuged at 10,000×g for 30 minutes at 4° C. Endogenous or transiently expressed proteins were immunoprecipitated with corresponding antibodies immobilized on protein A-Sepharose beads (Amersham Biosciences) for 3 hours at 4° C. The immune complexes were then washed once with Tris-buffered saline containing 0.05% Tween 20 and the Wash Buffer 1 (50 mM HEPES [pH 7.5], 40 mM NaCl, and 2 mM EDTA) with 1% Triton X-100, Wash Buffer 1 with 500 mM LiCl and 0.5% Triton X-100, Wash Buffer 1 with 500 mM LiCl, and Wash Buffer 2 (50 mM HEPES [pH 7.5] and 150 mM NaCl). For Raptor or Rictor immunoprecipitation studies, cells were lysed in ice-cold Buffer B (Buffer A with 0.3% CHAPS instead of Triton X-100). The mTOR immunoprecipitates were washed four times in Buffer B and twice in Wash Buffer 2. The immune complexes were used for immunoblotting or for in vitro kinase reactions.

Example 4

Identification of mTOR Beta

Figure 4:
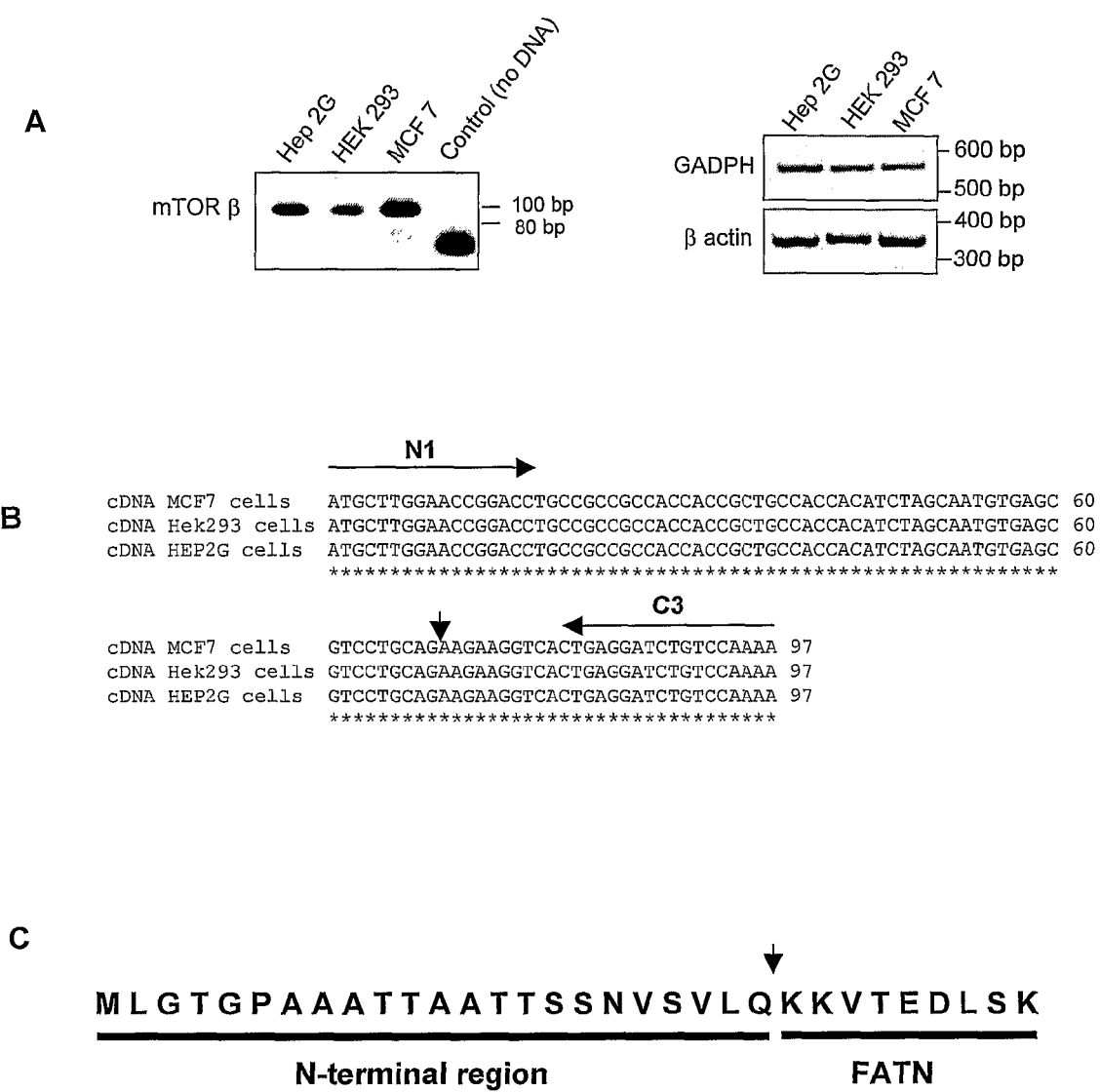
FIG. 4 shows the identification of potential mTOR splice variant in human cell lines by PCR.

To prove the existence of mTOR splice form(s), a PCR-based search for corresponding cDNAs by employing a panel of mTOR specific oligonucleotides and several human cell lines was carried out. In this analysis, Hek293 and MCF7 lines were used where a potential splice variant was observed. In addition, the hepatoma cell line Hep2G was also examined, since liver was found to possess several potential mTOR splice variants in Northern and Western blotting. Initially, total RNA was purified from exponentially growing cells using SV Total RNA Isolation System (Promega). Then, equal amounts of RNA purified from each cell line were converted into the first strand cDNA by using ReverAid H Minus First Strand cDNA Synthesis Kit (Fermentas). The quality of generated first strand cDNAs was tested by PCR amplification of actin and GADPH fragments. FIG. 4 shows that nearly equal amount of PCR products for GADPH (570 bp) and β-actin (350 bp) were PCR amplified from cDNA preparations of all cell lines. Extensive PCR analysis of generated first strand cDNAs with various sets of mTOR specific primers produced a panel of amplified fragments. The most prominent bands were excised from the gel and sequenced. Among obtained mTOR sequences, one mTOR sequence which contained a potential splice variant, was identified. This PCR fragment of approximately 100 bp was amplified with the N-terminal primer (N1, ATGCTTGGAACCGGAC-CTGCCG (SEQ ID NO: 5)) and the second primer, located in the end of FATN domain (C3, TTTGGACAGATCCTCAGT-GACCT (SEQ ID NO: 6)). It is important to note that this PCR product was specifically amplified from all three cell lines (see FIG. 4A). As shown in FIG. 4B, the amplified fragments contain sequences corresponding to the N-terminal region and the FATN domain of mTOR. The translation of generated sequences clearly indicates the continuation of the reading frame at the point of a splice site (see FIG. 4C). This splice form of mTOR (mTOR beta) has the potential to encode a protein of 706 amino acids in length, consisting of the extreme N-terminal 23 amino acids and a stretch of 683 amino acids from the C-terminus of mTOR.

In order to obtain the full-length coding sequence of this potential mTOR splice form, PCR amplifications from generated first strand cDNAs using the extreme N1 (ATGCTTG-GAACCGGACCTGCCG (SEQ ID NO: 7)) and C1 (TTAC-CAGAAAGGGCACCA (SEQ ID NO: 8)) mTOR specific primers were carried out. By this approach, to a band of approximately 2.3 Kb was amplified from Hek293 first strand cDNA. Initial sequence analysis of the amplified band from the N- and the C-terminal ends confirmed the existence of the predicted splice variant of mTOR.

The amplified PCR product was then fully sequenced and its nucleotide sequence (SEQ ID NO: 1)) was found to have mTORβ specific intron/exon at nucleotides 68 to 72. The obtained sequence has an open reading frame capable to encode a protein of 706 amino residues (SEQ ID NO: 1). The position of a splice fusion between the N-terminal (1-23 aa) and the C-terminal (1867-2549 aa) of mTORα is indicated by an arrow.

The identified splice form of mTOR was termed "mTOR beta (mTORβ)" and the full-length protein (mTOR alpha (mTORα)). In contrast to the full-length mTORα, the mTORβ splice form lacks all HEAT domains and the main part of the FATN domain (see FIG. 5). The HEAT domains have been implicated in mediating protein-protein interactions. In mTOR, the sequences corresponding to HEAT domains were found to interact with Raptor and Rictor, which are key players in mTOR signaling. Moreover, the sequences within the HEAT domain region were shown to localize mTOR to endoplasmic reticulum and Golgi apparatus. Recent studies indicated that FAT domains possess HEAT-like structures and might be also involved in protein-protein interactions. The mTORβ possesses intact FRB (FKBP12/ Rapamycin Binding), kinase, and FATC domains. The presence of these domains suggests that mTORβ could serve as a protein kinase and its function could be regulated by Rapamycin and its analogs. In addition, mTORβ contains 23 amino acids of unknown function from the extreme N-terminus and the C-terminal part of FATN domain. Bioinformatic analysis of the FATN C-terminal region point towards the presence of a HEAT-like domain, which might facilitate the interactions with regulatory proteins, such as Rictor and Raptor.

Example 5 mTORβ Regulation and Cellular Function

Following the identification and cloning of mTORβ, the work on the investigation of its regulation and cellular functions was initiated. Initially, the full-length of mTORβ was cloned in pcDNA3.1 expression vector in frame with the N-terminal FLAG-tag epitope. To examine the level of expression, molecular weight, and regulation of FLAG-mTORβ, Hek293 cells were transiently transfected with pcDNA3.1 or pcDNA3.1/FLAG-mTORβ. One day after transfection, cells were serum-starved for 36 hours and incubated in the presence or absence of Rapamycin for 30 minute. After serum stimulation for one hour, cells were lysed and the lysates were used for Western blotting or immunoprecipitation. When the supernatants of lysed cells were immunoblotted with anti-mTOR polyclonal antibody (Cell Signalling), it was clear that pcDNA3.1/FLAG-mTORβ plasmid directs the expression of the protein with the molecular weight of approximately 80 kDa (see FIG. 6A, lower panel). The expression of endogenous mTORβ is evidently observed in Hek293 cells transfected with pcDNA3.1 or pcDNA3.1/ FLAG-mTORβ. Due to the presence of a FLAG epitope, the mobility of FLAG-mTORβ is slightly slower when compared to that of endogenous mTORβ. This analysis also showed that starvation/stimulation of cells with serum do no affect the level or gel mobility of both endogenous and overexpressed mTORβ. No significant changes were also observed after Rapamycin treatment.

Figure 6:
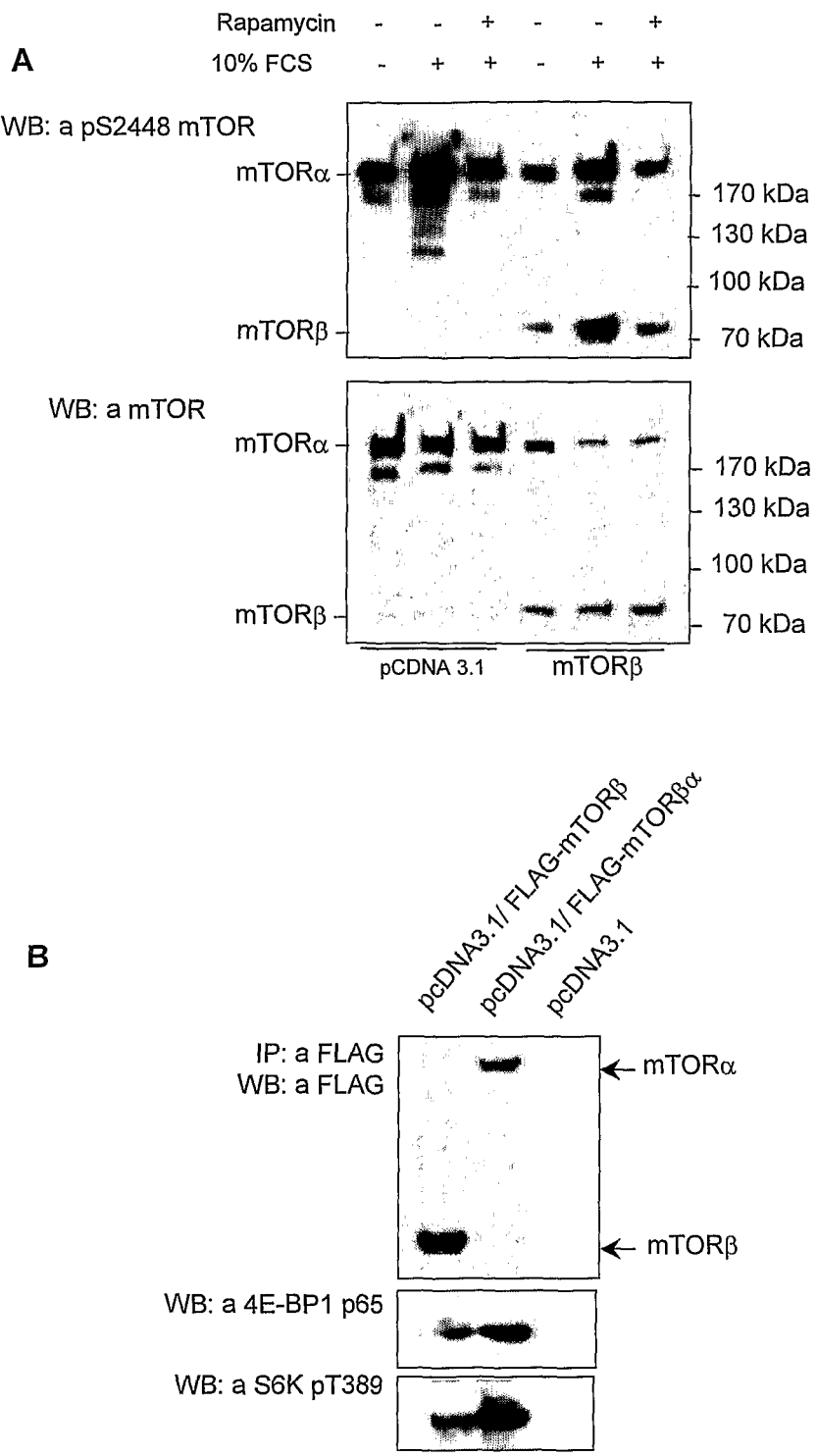
FIG. 6 shows that mTORβ is phosphorylated at a serine residue corresponding to Ser2448 of the entire mTORα amino acid sequence in response to serum stimulation and phosphorylates S6K1 and 4E-BP1 in in vitro kinase assay.

Stimulation of cells with serum or growth factors, such as IGF1 is known to induce phosphorylation of mTORα on S2448. Originally, the phosphorylation of mTORα at S2448 was found to be mediated by PKB/Akt. However, recent studies have provided strong evidence for the involvement of S6K in phosphorylating S2448. To find whether mTORβ is phosphorylated at a serine residue corresponding to S2448 of the entire mTORα amino acid in response to serum stimulation, the obtained lysates from the above experiment were probed with S2448 phosphospecific antibody. As shown in FIG. 6A (upper panel), the phosphorylation of endogenous and overexpressed mTORβ at a serine residue corresponding to S2448 of the entire mTORα amino acid sequence is strongly induced by serum stimulation. Moreover, this phosphorylation event is sensitive to Rapamycin. The obtained data demonstrate that similarly to mTORα, the phosphorylation of mTORβ at a serine residue corresponding to S2448 of the entire mTORα amino acid sequence is induced in response to serum stimulation and is sensitive to Rapamycin.

Is mTORβ able to phosphorylate S6K and 4E-BP1, which are the main physiological substrates for mTORα? To answer this question, FLAG-mTORβ or FLAG-TORα were immunoprecipitated from transiently transfected Hek293 cells. The immune complexes were then used in mTOR kinase reactions, containing cold ATP and recombinant 4E-BP1 or His-S6K1C. The kinase reactions were resolved by SDS-PAGE and immunoblotted with phosphospecific antibodies pT389-S6K1 and pS65-4E-BP1. FIG. 6B undoubtedly demonstrates that mTORβ can phosphorylate both S6K1 and 4E-BP1 in vitro, but to a lesser extent than mTORα.

Figure 7:
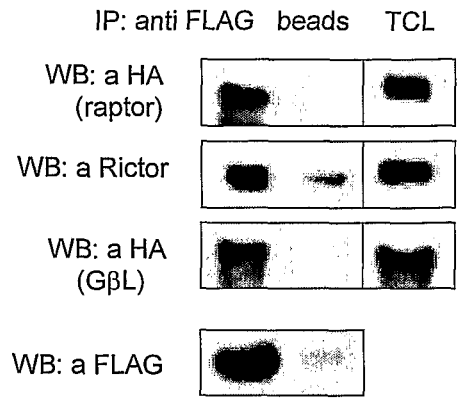
FIG. 7 shows the specific interaction of mTORβ with Raptor, Rictor, and GβL. HEK293 cells were transfected with pcDNA3.1-mTORβ-FLAG and pRK-Raptor-HA or pcDNA3.1-mTORβ-FLAG and pRK-Rictor-Myc or pcDNA3.1-mTORβ-FLAG and pcRK-GβL. The supernatants of lysed cells were immunoprecipitated with anti-FLAG antibody or control nonspecific antibody. The immune complexes or total cell lysates from transfected cells (15 μg) were resolved by SDS-PAGE and probed in Western blotting with anti-HA, anti-Rictor, or anti-GβL antibodies.

Studies from various laboratories indicated that mTOR requires binding partners Raptor and Rictor for the phosphorylation of its downstream substrates: S6K, 4E-BP1 and PKB/Akt. Taking this into account, the interaction of mTORβ with known mTOR binding partners was tested. In this study, HEK293 cells were transiently transfected with pcDNA3.1/FLAG-mTORβ and pRK/Raptor-HA or pcDNA3.1/FLAG-mTORβ and pRK/Rictor-Myc or pcDNA3.1/FLAG-mTORβ and pcRK-GβL. The supernatants of lysed cells were immunoprecipitated with anti-FLAG monoclonal or control non-specific antibody. The immune complexes or total cell lysates from transfected cells were resolved by SDS-PAGE and immunoblotted with various antibodies. FIG. 7 clearly shows that exogenously expressed Raptor, Rictor, and GβL form specific complexes with mTORβ in vivo. The specificity of interaction was tested by using irrelevant antibody in the immunoprecipitation assay. Thus, similarly to the full-length mTORα, the splice form is also capable to associate with Raptor, Rictor, and GβL. It can also phosphorylate S6K1 and 4E-BP1 in vitro.

Figure 8:
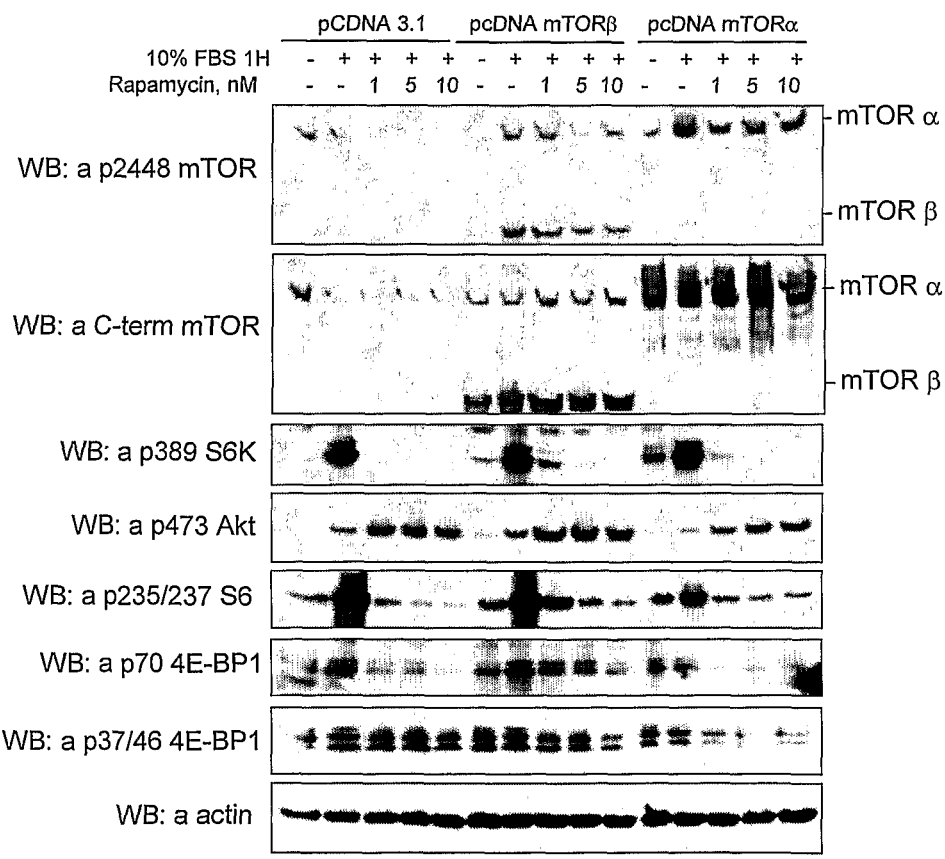
FIG. 8 shows that mTORβ is less sensitive to Rapamycin in comparison to mTORα. HEK293 cells were transfected with pcDNA3.1, pcDNA 3.1 mTORβ, or pcDNA 3.1 mTORα. One day later, cells were starved for 24 hours and then stimulated with 10% serum for 1 hour. Various concentrations of Rapamycin were added 30 minutes before stimulation. Cells were lysed, resolved by SDS-PAGE and immunoblotted with the C-terminal mTOR antibody, anti-actin and different phosphospecific antibodies.

As mentioned above, mTORβ possesses an intact FRB domain. Therefore, it was interesting to compare the sensitivity of mTORα and mTORβ to Rapamycin. In this study, HEK293 cells were transiently transfected with pcDNA 3.1/FLAG-mTORβ, pcDNA 3.1/FLAG-mTORα, or pcDNA3.1. One day later, cells were starved for 24 hours and stimulated with 10% FCS for one (1) hour. Various concentrations of Rapamycin (1 nM, 5 nM and 10 nM) were added 30 minutes before serum stimulation. The supernatants of lysed cells were resolved by SDS-PAGE and immunoblotted with various antibodies. The expression of mTORα and mTORβ was confirmed by immunoblotting with the C-terminal polyclonal mTOR antibody (see FIG. 8). Probing the membrane with a panel of phosphospecific antibodies directed against known mTOR phosphorylation sites in S6K1 (pT389) and 4E-BP1 (pS70, pS37/46) indicated that cells expressing mTORβ are less sensitive to Rapamycin, when compared to cells transfected with vector alone or pcDNA31/mTORα. Notably, the sensitivity was more obvious in cells treated with low doses of Rapamycin, such as 1 nM.

Figure 9:
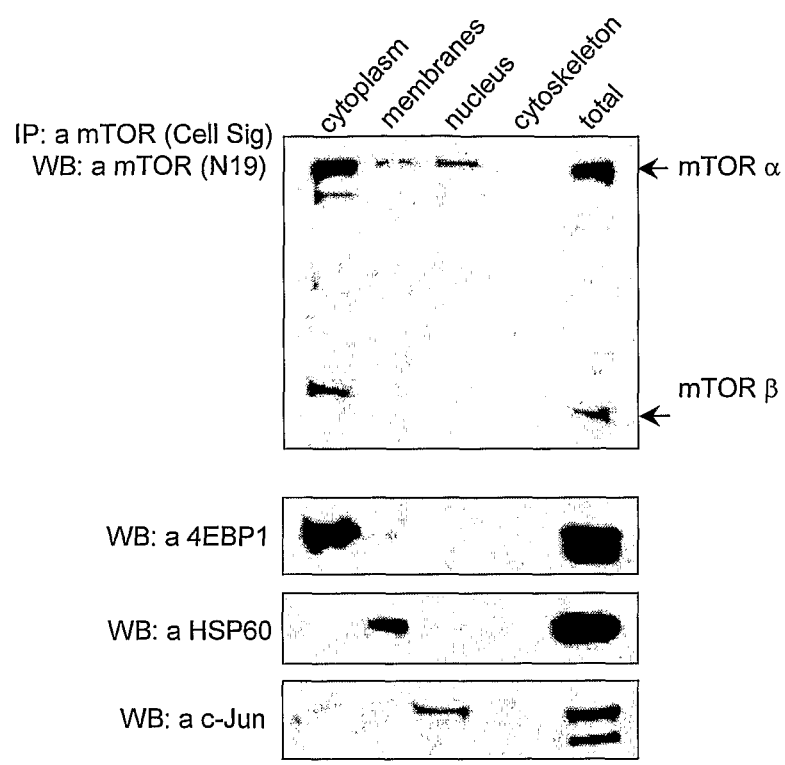
FIG. 9 shows the subcellular localization of mTORβ. Exponentially growing HEK293 cells were fractionated using ProteoExstract Extraction kit (Calbiochem). mTORα and mTORβ were immunoprecipitated from all fractions using anti-mTOR C-terminal antibodies and immune complexes resolved by SDS-PAGE and immunoblotted with anti-mTOR N-terminal antibodies. Anti-4EBP1, HSP60, and c-Jun antibodies were used as controls for cytoplasm, membrane, and nuclear fractions, respectively.

Previous studies found mTORα mainly in membrane fractions of endoplasmic reticulum and Golgi apparatus. Furthermore, mTOR was also observed on the outer mitochondrial membrane and in the nucleus. Sequences located in the HEAT domain region of full-length mTOR (HEAT domain 18 and 19) have been implicated in mediating its membrane localization. Taking into account that HEAT and FATN domains are not present in mTORβ, it was interesting to examine its subcellular localization by fractionation. Exponentially growing HEK293 cells were fractionated using ProteoExstract Extraction kit (Calbiochem). Both, mTORα and mTORβ were immunoprecipitated from all fractions using anti-mTOR C-terminal antibodies. The immune complexes were resolved by SDS-PAGE and immunoblotted with anti-mTOR N-terminal antibodies. As expected, mTORα is detected in obtained cytoplasmic, nuclear and membrane fractions. In contrast to that, mTOR is predominantly localized in the cytoplasm (see FIG. 9). The quality of prepared subcellular fractions was analyzed by immunoblotting with anti-4E-BP1, HSP60, and c-Jun antibodies. Currently immunofluorescent analysis is being employed to study subcellular localization of Myc-mTORα and mTORβ in transiently transfected Hek293 cells (starved/stimulated and in response to cellular stresses).

Figure 10:
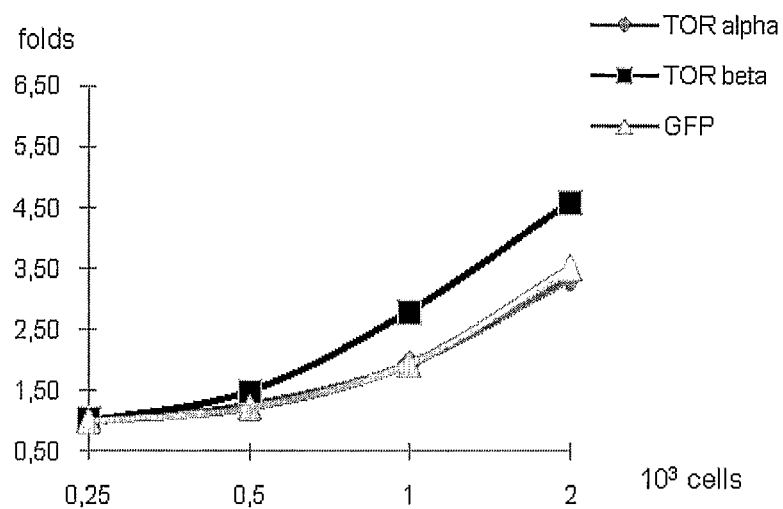
FIG. 10 shows that overexpression of mTORβ but not mTORα induces cell proliferation. Hek293 stable cell lines, over-expressing mTORβ wt, mTORα wt or EGFP were seeded into a 96 well plate at various densities (250, 500, 1000 and 2000 cells per well) and grown under standard conditions for 7 days. Cell numbers were than measured in each well by a Resosurin based assay. Normalized growth curves for each cell line were calculated using data from six independent experiments (A). Western blot analysis of total cell lysates of stable cell lines with antibodies to c-myc and its transcription targets (B). The level of proteins was densitometrically measured, actin normalized and folds were calculated against EGFP expressing stable cell line (C).
Figure 10:
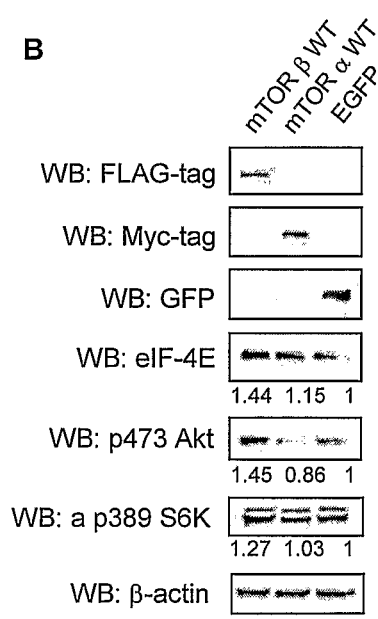
Figure 10:
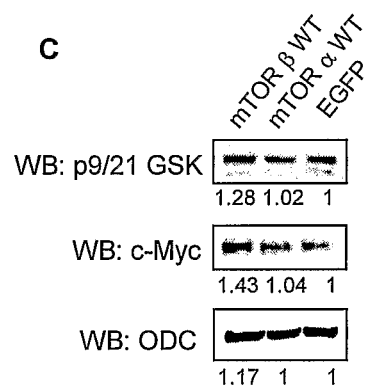

To further investigate the role of mTORβ in the regulation of cellular processes, Hek293 stable cell lines, overexpressing mTORβ wild type and mTORα wild type, were generated. In addition, a cell line over-expressing EGFP (Enhanced Green Fluorescent Protein), which could be used as a control in mTORβ studies, has also developed. Initial examination of generated cell lines indicated that cells expressing wild type mTORβ grow faster, when compared with mTORα or GFP expressing cells. Taking this into account, the proliferation rate of generated stable cell lines using a cell proliferation assay from Promega was investigated. Stable cell lines, overexpressing mTORβ wt, mTORα wt or EGFP were seeded into a 96 well plate at various densities and grown under standard conditions for 7 days. Cell numbers were than measured in each well by Resosurin based assay. In six independent studies, it was found that mTORβ expressing cells proliferate faster in comparison to control cells (see FIG. 10). In contrast, mTORα wt expressing cells showed no difference in proliferation compared to control cells. This confirms a role of mTORβ, but not mTORα in regulation of cell proliferation.

Figure 11:
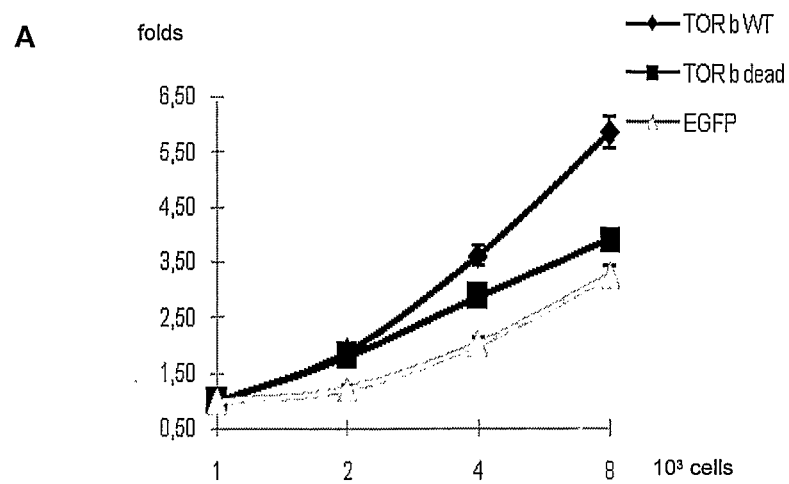
FIG. 11 shows that mTORβ kinase activity is required for the induction of proliferation. HEK293 stable cell lines, overexpressing mTORβ wt, mTORβ kinase-dead or EGFP were seeded into 96 well plate at various densities (1000, 2000, 4000 and 8000 cells per well) and grown under standard conditions for 5 days. Cell numbers were then measured in each well by Resazurin based assay. Normalized growth curves for each cell line were calculated using data from six independent experiments (A). Western blot analysis of total cell lysates of stable cell lines with antibodies to c-myc and its transcription targets. The level of proteins was densitometrically measured, actin normalized and folds were calculated against EGFP expressing stable cell line (B).
Figure 11:
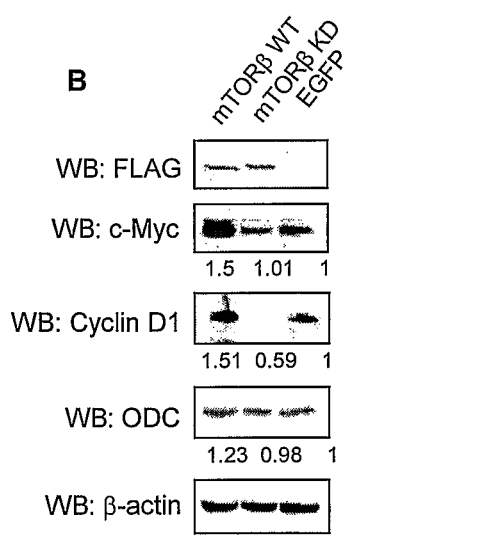

To investigate whether mTORβ kinase activity has a role in the regulation of cell proliferation, a similar experiment was carried out in Hek293 cell lines, overexpressing mTORβ wild type, mTORβ kinase dead (KD) mutant or EGFP. Cells were seeded into a 96 well plate at various densities and grown under standard conditions for 5 days. Cell numbers were then measured in each well by Resazurin based assay. In six independent studies, it was found that mTORβ expressing cells proliferate approximately 1.6 times faster in comparison to control cells (see FIG. 11). The obtained data also indicate that mTORβ KD mutant does not have a dominant negative effect on cell proliferation, when expressed in Hek293 cells. It exhibits a slightly opposite effect, as mTORβ KD overexpressing cells grew to some extent faster when compared with EGFP cells.

It is further thought that the induction of cell proliferation by mTORβ could be transduced by various signaling pathways. One of those pathways, signaling via the proto-oncogene Myc was examined. The proto-oncogene Myc is known to affect growth, proliferation, differentiation, and apoptosis of cells through its ability to regulate the transcription of a vast number of genes. cMyc has been also implicated in the regulation of tumor progression, including genetic stability, migration, and angiogenesis. The expression and function of cMyc protein is therefore tightly controlled. Indeed many different pathways and factors have been identified that modulate cMyc expression at the level of transcription and translation, and its protein function through post-translational modifications. In regulating of cell proliferation, c-Myc controls the expression of genes, which participate in G1/S transition of the cell cycle. Signalling via mTOR pathway makes a major contribution to the cell cycle progression at G1/S stage. Moreover, Rapamycin is a known inhibitor of the G1/S transition of the cell cycle.

To test whether cMyc is involved in mTORβ-induced proliferation, HEK293 cells were transiently transfected with pEGFP, pcDNA 3.1/mTORβ wt, pcDNA 3.1/mTORβ dead mutant, or pcDNA 3.1/mTORα wt. Two days after transfection cells were lysed, separated by SDS-PAGE and immunoblotted with antibodies to c-myc and its transcription targets (e.g. anti-Myc (9E10) monoclonal antibody). The results presented in FIG. 10B, clearly demonstrate that overexpression of mTORβ, but not mTORα leads to a significant increase in c-Myc protein level. The induction of c-Myc translation is dependent on mTORβ kinase activity, as a kinase dead mutant of mTORβ does not stimulate c-Myc expression (FIG. 11B). The expression level of transiently expressed mTORα, mTORβ wt, and KD mutant was monitored by immunoblotting with the C-term mTOR antibody. Overexpression of mTORβ wt was found to increases the level of Myc expression. It was also found that Hek293 cells, overexpressing mTORβ recover from Sorbitol-induced stress much faster than mTORα overexpressing cells.

Figure 12:
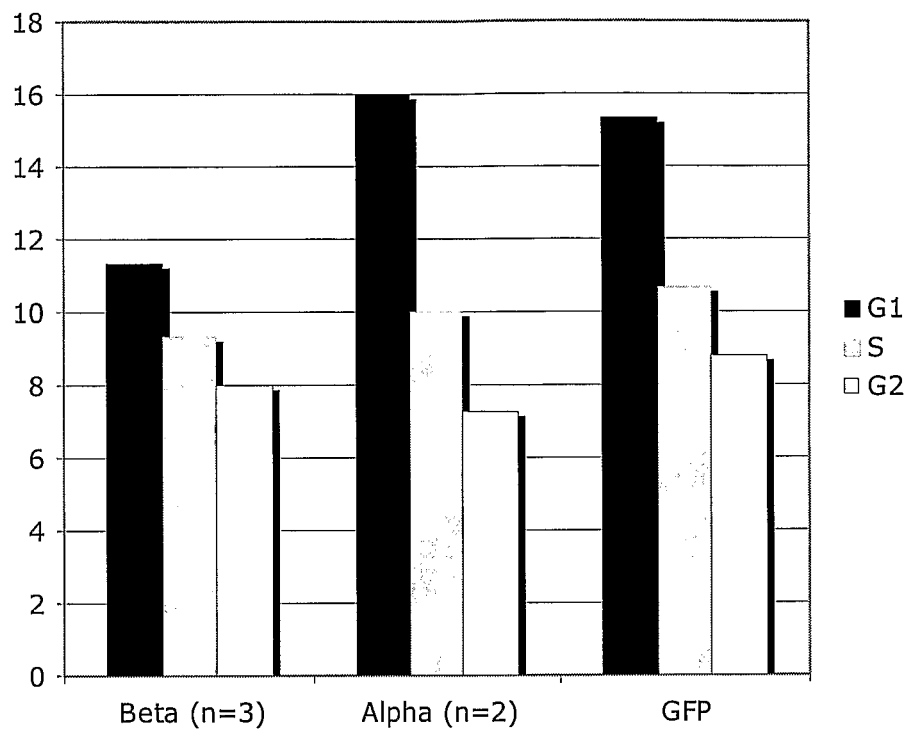
FIG. 12 shows that mTORβ is critical for G1 progression of the cell cycle. HEK293 cells stably overexpressing mTORβ, mTORα or EGFP were pulse labeled with BrdU for 30 minutes and chased every 2 hours for 24 hours. The incorporation of BrdU was measured by FACS analysis. Duration of G1, S and G2 phases of cell cycle observed for each cell line is presented on graph. SD, p=0.05.

To further investigate the role of mTORβ in the cell cycle, Hek293 cells overexpressing mTORβ, mTORα or EGFP were pulse labeled with BrdU for 30 minutes and chased every 2 hours for 24 hours. Incorporation of BrdU into the cells was measured by FACS analysis. The duration of the G1, S and G2 phases of cell cycle observed for each cell line was determined (see FIG. 12). The duration of S and G2 phases were similar in all three cell groups. However, the duration of the G1 phase was shorter in the mTORβ overexpressing cells than in the mTORα or control cells. This suggests that mTORβ is critical for G1 progression of the cell cycle.

Figure 13:
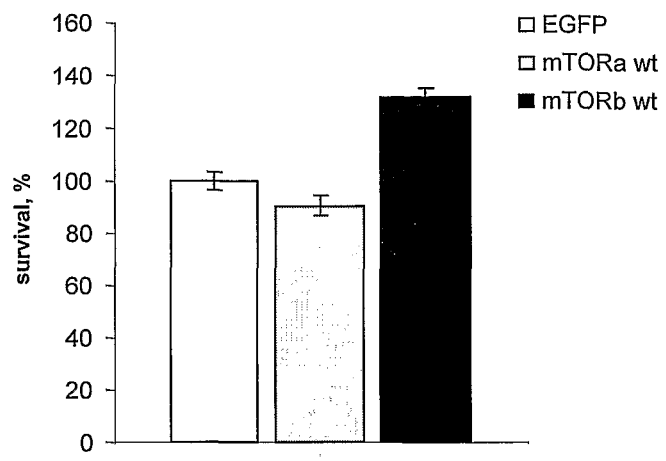
FIG. 13 shows that overexpression of mTORβ protects cells from starvation-induced cell death (A). mTORβ kinase activity is required for mediating pro-survival effect (B). Hek293 stable cell lines, overexpressing mTORβ wt, mTORα wt, mTORβ kinase dead or EGFP were serum starved for 60 hours. Cell survival was assessed by the Trypan Blue dye exclusion assay. Data are means±SE of 5 experiments. * P value≤0.01.
Figure 13:
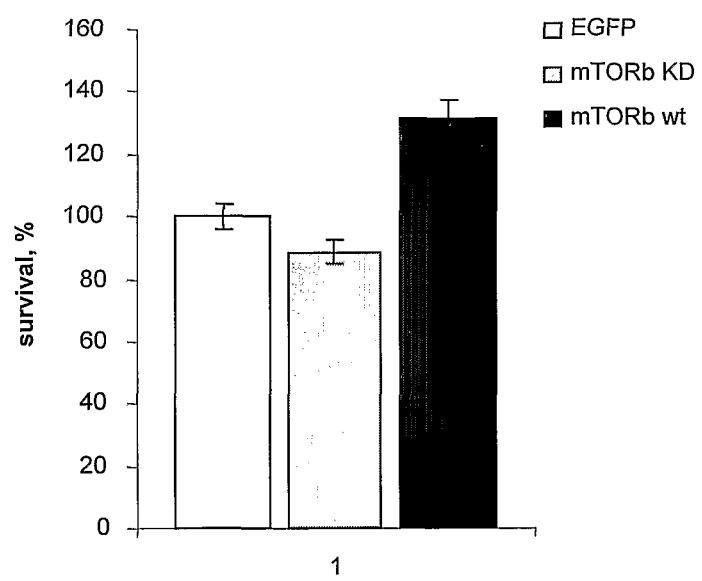

The effects of mTORβ in serum starved cells were also assessed. Hek293 stable cell lines, overexpressing mTORβ wt, mTORα wt, mTORβ kinase dead or EGFP were serum starved for 60 hours. Cell survival was assessed by the Trypan Blue dye exclusion assay. It was found that overexpression of mTORβ wt protected cells from starvation induced cell death (see FIG. 13A) and that mTORβ kinase activity is required for mediating this effect (see FIG. 13B).

Figure 14:
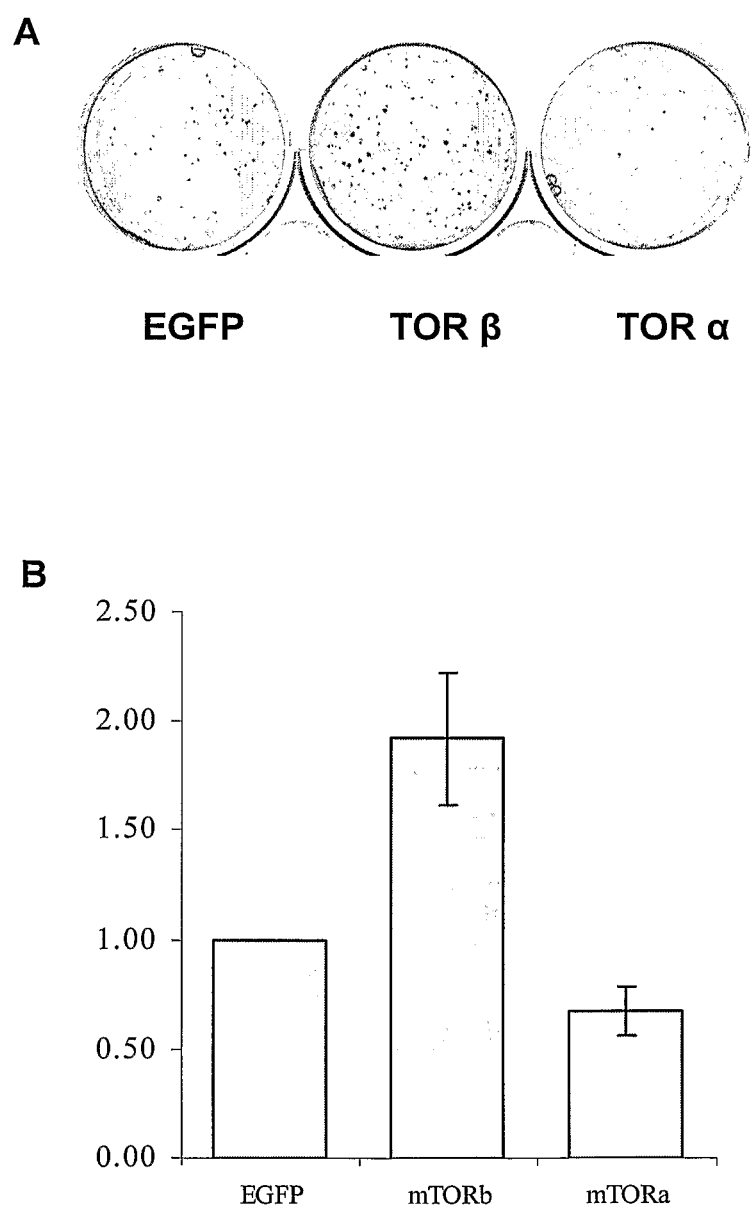
FIG. 14 shows that mTORβ overexpression leads to increase in cell oncogenic potential. HEK293 cells stably overexpressing mTORβ, mTORα or EGFP were plated in a thin layer of agarose in culture medium. After 14 days, colonies were stained using MTT (A). Colonies were counted using Quantity One Software (Bio-Rad) and folds were plotted (B). Data are means±SE of 4 experiments. * P value≤0.01.

To further investigate the effect of mTORβ expression on cell oncogenic potential, Hek293 cells stably overexpressing mTORβ, mTORα or EGFP were plated in a thin layer of agarose in culture medium. After 14 days, colonies were stained using MTT (see FIG. 14A). Colonies were counted using quantity 1 software (Bio-Rad) and folds were plotted (see FIG. 14B). It was found that mTORβ overexpression led to an increase in cell oncogenic potential compared with those cells overexpressing mTORα and control cells.

Experimental Procedures for In Vitro Kinase Assay mTOR in vitro kinase assay was performed as published previously (Kim et al. 2002). Briefly, the kinase assay was performed in 30 µl at 30° C. for 40 minutes and contained about a quarter of the washed mTOR immunoprecipitates from 5×10⁶ HEK293 cells, 1 µg of a 4E-BP1 (Calbiochem) or 0.5 µg of recombinant His-S6K1C, 25 mM HEPES-KOH (pH 7.4), 50 mM KCl, 20% glycerol, 10 mM $MgCl_2$, 4 mM $MnCl_2$, 1 mM DTT, and 50 µM ATP. The reactions were stopped by adding 5× sample buffer and resolved by SDS-PAGE and analyzed by immunoblotting.

Experimental Procedures for Immunoblot Analysis

Immune complexes or total cell lysates were separated by SDS-PAGE, transferred onto polyvinylidene difluoride membrane (PVDF) and incubated for 1 hour with blocking solution (5% milk, Tris-buffered saline/Tween 0.1%). Blocked membranes were then probed overnight with primary antibodies at 4° C. After extensive washing with Tris-buffered saline with 0.1% Tween, the membranes were incubated for 1 hour with secondary horseradish peroxidase-conjugated antibody at RT. The antigen-antibody complexes were detected using the ECL system (Millipore). When immunoblots had to be re-probed, the membranes were initially stripped (Restore Western Stripping Reagent, Pierce) and incubated with another type of primary antibody.

Experimental Procedures for Subcellular Fractionation

Subcellular fractionation of HEK293 cells was performed using ProteoExstract Extraction kit (Calbiochem) as recommended by manufacturer. mTORα and mTORβ were immunoprecipitated from all fractions using anti-mTOR C-terminal antibodies. Immune complexes were resolved by SDS-PAGE and immunoblotted with anti-mTOR N-terminal antibody. Anti-4E-BP1, HSP60 and c-Jun antibodies were used as controls for cytoplasmic, membrane and nuclear fractions respectively.

Experimental Procedures for Stable Cell Lines Production and Cell Proliferation Assay Stable cell lines overexpressing wild type and kinase dead mTORβ were produced by transfecting linearized pcDNA 3.1/FLAG-Tor β wt or pcDNA 3.1 FLAG Tor β dead vectors in to HEK293 cells. Cell lines were selected for 10 days on 500 µg/ml genetecin as recommended by manufacturer (Invitrogen). For cell proliferation assay, Hek293 stable cell lines, overexpressing mTOR β wt, mTOR β kinase dead and EGFP were seeded into 96 well plate at various density (250, 500, 1000 and 2000 cell per well) and grown under standard conditions for 5 days. Cell numbers were than measured in each well by Resosurin based assay (Cell Titer Blue Promega)) as recommended by the manufacturer. Normalized growth curves for each cell line were calculated using data from at least six independent experiments).

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

The invention claimed is:

1. An isolated mTORbeta polypeptide which phosphorylates S6K1 and/or 4E-BP1 selected from the group consisting of:

(a) an isolated polypeptide comprising the amino acid sequence of SEQ ID NO: 2; and
(b) an isolated polypeptide comprising the amino acid sequence encoded by SEQ ID NO: 1.

* * * * *

UNITED STATES PATENT AND TRADEMARK OFFICE
CERTIFICATE OF CORRECTION

PATENT NO. : 8,669,347 B2  
APPLICATION NO. : 12/598394  
DATED : March 11, 2014  
INVENTOR(S) : Nemazanyy et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 916 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 10

<210> SEQ ID NO 1
<211> LENGTH: 2121
<212> TYPE: DNA
<213> ORGANISM: Homo sapiens

<400> SEQUENCE: 1

```
atgcttggaa ccggacctgc cgccgccacc accgctgcca ccacatctag caatgtgagc      60
gtcctgcaga agaaggtcac tgaggatctg tccaaaaccc tcctgatgta cacggtgcct     120
gccgtccagg gcttcttccg ttccatctcc ttgtcacgag gcaacaacct ccaggataca     180
ctcagagttc tcaccttatg gtttgattat ggtcactggc cagatgtcaa tgaggcctta     240
gtggaggggg tgaaagccat ccagattgat acctggctac aggttatacc tcagctcatt     300
```

```
gcaagaattg atacgccag accctttggtg ggacgtctca ttcaccagct tctcacagac    360
attggtcggt accaccccca ggccctcatc tacccactga cagtggcttc taagtctacc    420
acgacagccc ggcacaatgc agccaacaag attctgaaga acatgtgtga gcacagcaac    480
accctggtcc agcaggccat gatggtgagc gaggagctga tccgagtggc catcctctgg    540
catgagatgt ggcatgaagg cctggaagag gcatctcgtt tgtactttgg ggaaaggaac    600
gtgaaaggca tgtttgaggt gctggagccc ttgcatgcta tgatggaacg gggcccccag    660
actctgaagg aaacatcctt taatcaggcc tatggtcgag atttaatgga ggcccaagag    720
tggtgcagga agtacatgaa atcagggaat gtcaaggacc tcacccaagc ctgggacctc    780
tattatcatg tgttccgacg aatctcaaag cagctgcctc agctcacatc cttagagctg    840
caatatgttt ccccaaaaact tctgatgtgc cgggaccttg aattggctgt gccaggaaca    900
tatgacccca accagccaat cattcgcatt cagtccatag caccgtcttt gcaagtcatc    960
acatccaagc agaggccccg gaaattgaca cttatgggca gcaacggaca tgagtttgtt   1020
ttccttctaa aaggccatga agatctgcgc caggatgagc gtgtgatgca gctcttcggc   1080
ctggttaaca cccttctggc caatgaccca acatctcttc ggaaaaacct cagcatccag   1140
agatacgctg tcatcccttt atcgaccaac tcgggcctca ttggctgggt tccccactgt   1200
gacacactgc acgccctcat ccgggactac agggagaaga gaagatcct tctcaacatc   1260 gagcatcgca tcatgttgcg gatggctccg gactatgacc acttgactct gatgcagaag   1320
gtggaggtgt ttgagcatgc cgtcaataat acagctgggg acgacctggc caagctgctg   1380
tggctgaaaa gccccagctc cgaggtgtgg tttgaccgaa gaaccaatta tacccgttct   1440
ttagcggtca tgtcaatggt tgggtatatt ttaggcctgg gagatagaca cccatccaac   1500
ctgatgctgg accgtctgag tgggaagatc ctgcacattg actttgggga ctgctttgag   1560
gttgctatga cccgagagaa gtttccagag aagattccat ttagactaac aagaatgttg   1620
accaatgcta tggaggttac aggcctggat ggcaactaca gaatcacatg ccacacagtg   1680
atggaggtgc tgcgagagca caaggacagt gtcatggccg tgctggaagc ctttgtctat   1740
gaccccttgc tgaactggag gctgatggac acaaatacca aaggcaacaa gcgatcccga   1800
acgaggacgg attcctactc tgctggccag tcagtcgaaa ttttggacgg tgtgaacttt   1860
ggagagccag cccataagaa aacgggggacc acagtgccag aatctattca ttctttcatt   1920
ggagacggtt tggtgaaacc agaggcccta aataagaaag ctatccagat tattaacagg   1980
gttcgagata agctcactgg tcgggacttc tctcatgatg acacttttgga tgttccaacg   2040 caagttgagc tgctcatcaa acaagcgaca tcccatgaaa acctctgcca gtgctatatt   2100
ggctggtgcc ctttctggta a                                              2121
```

<210> SEQ ID NO 2
<211> LENGTH: 706
<212> TYPE: PRT
<213> ORGANISM: Homo sapiens

<400> SEQUENCE: 2

```
Met Leu Gly Thr Gly Pro Ala Ala Thr Thr Ala Ala Thr Thr Ser
 1               5                  10                  15

Ser Asn Val Ser Val Leu Gln Lys Lys Val Thr Glu Asp Leu Ser Lys
                20                  25                  30

Thr Leu Leu Met Tyr Thr Val Pro Ala Val Gln Gly Phe Phe Arg Ser
            35                  40                  45
```

-continued

```
Ile Ser Leu Ser Arg Gly Asn Asn Leu Gln Asp Thr Leu Arg Val Leu
     50                  55                  60

Thr Leu Trp Phe Asp Tyr Gly His Trp Pro Asp Val Asn Glu Ala Leu
 65                  70                  75                  80

Val Glu Gly Val Lys Ala Ile Gln Ile Asp Thr Trp Leu Gln Val Ile
                 85                  90                  95

Pro Gln Leu Ile Ala Arg Ile Asp Thr Pro Arg Pro Leu Val Gly Arg
                100                 105                 110

Leu Ile His Gln Leu Leu Thr Asp Ile Gly Arg Tyr His Pro Gln Ala
                115                 120                 125

Leu Ile Tyr Pro Leu Thr Val Ala Ser Lys Ser Thr Thr Thr Ala Arg
                130                 135                 140

His Asn Ala Ala Asn Lys Ile Leu Lys Asn Met Cys Glu His Ser Asn
145                 150                 155                 160

Thr Leu Val Gln Gln Ala Met Met Val Ser Glu Leu Ile Arg Val
                165                 170                 175

Ala Ile Leu Trp His Glu Met Trp His Gly Leu Glu Glu Ala Ser
                180                 185                 190

Arg Leu Tyr Phe Gly Glu Arg Asn Val Lys Gly Met Phe Glu Val Leu
                195                 200                 205

Glu Pro Leu His Ala Met Met Glu Arg Gly Pro Gln Thr Leu Lys Glu
                210                 215                 220

Thr Ser Phe Asn Gln Ala Tyr Gly Arg Asp Leu Met Glu Ala Gln Glu
225                 230                 235                 240

Trp Cys Arg Lys Tyr Met Lys Ser Gly Asn Val Lys Asp Leu Thr Gln
                245                 250                 255

Ala Trp Asp Leu Tyr Tyr His Val Phe Arg Arg Ile Ser Lys Gln Leu
                260                 265                 270

Pro Gln Leu Thr Ser Leu Glu Leu Gln Tyr Val Ser Pro Lys Leu Leu
                275                 280                 285

Met Cys Arg Asp Leu Glu Leu Ala Val Pro Gly Thr Tyr Asp Pro Asn
                290                 295                 300

Gln Pro Ile Ile Arg Ile Gln Ser Ile Ala Pro Ser Leu Gln Val Ile
305                 310                 315                 320

Thr Ser Lys Gln Arg Pro Arg Lys Leu Thr Leu Met Gly Ser Asn Gly
                325                 330                 335

His Glu Phe Val Phe Leu Leu Lys Gly His Glu Asp Leu Arg Gln Asp
                340                 345                 350

Glu Arg Val Met Gln Leu Phe Gly Leu Val Asn Thr Leu Leu Ala Asn
                355                 360                 365

Asp Pro Thr Ser Leu Arg Lys Asn Leu Ser Ile Gln Arg Tyr Ala Val
                370                 375                 380

Ile Pro Leu Ser Thr Asn Ser Gly Leu Ile Gly Trp Val Pro His Cys
385                 390                 395                 400

Asp Thr Leu His Ala Leu Ile Arg Asp Tyr Arg Glu Lys Lys Lys Ile
                405                 410                 415

Leu Leu Asn Ile Glu His Arg Ile Met Leu Arg Met Ala Pro Asp Tyr
                420                 425                 430

Asp His Leu Thr Leu Met Gln Lys Val Glu Val Phe Glu His Ala Val
                435                 440                 445

Asn Asn Thr Ala Gly Asp Asp Leu Ala Lys Leu Leu Trp Leu Lys Ser
                450                 455                 460

Pro Ser Ser Glu Val Trp Phe Asp Arg Arg Thr Asn Tyr Thr Arg Ser
465                 470                 475                 480
```

```
Leu Ala Val Met Ser Met Val Gly Tyr Ile Leu Gly Leu Gly Asp Arg
            485                 490                 495
His Pro Ser Asn Leu Met Leu Asp Arg Leu Ser Gly Lys Ile Leu His
            500                 505                 510
Ile Asp Phe Gly Asp Cys Phe Glu Val Ala Met Thr Arg Glu Lys Phe
            515                 520                 525
Pro Glu Lys Ile Pro Phe Arg Leu Thr Arg Met Leu Thr Asn Ala Met
            530                 535                 540
Glu Val Thr Gly Leu Asp Gly Asn Tyr Arg Ile Thr Cys His Thr Val
545                 550                 555                 560
Met Glu Val Leu Arg Glu His Lys Asp Ser Val Met Ala Val Leu Glu
            565                 570                 575
Ala Phe Val Tyr Asp Pro Leu Leu Asn Trp Arg Leu Met Asp Thr Asn
            580                 585                 590
Thr Lys Gly Asn Lys Arg Ser Arg Thr Arg Thr Asp Ser Tyr Ser Ala
            595                 600                 605
Gly Gln Ser Val Glu Ile Leu Asp Gly Val Glu Leu Gly Glu Pro Ala
            610                 615                 620
His Lys Lys Thr Gly Thr Thr Val Pro Glu Ser Ile His Ser Phe Ile
625                 630                 635                 640
Gly Asp Gly Leu Val Lys Pro Glu Ala Leu Asn Lys Lys Ala Ile Gln
            645                 650                 655
Ile Ile Asn Arg Val Arg Asp Lys Leu Thr Gly Arg Asp Phe Ser His
            660                 665                 670
Asp Asp Thr Leu Asp Val Pro Thr Gln Val Glu Leu Leu Ile Lys Gln
            675                 680                 685
Ala Thr Ser His Glu Asn Leu Cys Gln Cys Tyr Ile Gly Trp Cys Pro
            690                 695                 700
Phe Trp
705

<210> SEQ ID NO 3
<211> LENGTH: 7943
<212> TYPE: DNA
<213> ORGANISM: Homo sapiens

<400> SEQUENCE: 3
acggggcctg aagcggcggt accggtgctg gcggcggcag ctgaggcctt ggccgaagcc      60
gcgcgaacct cagggcaaga tgcttggaac cggacctgcc gccgccacca ccgctgccac     120
cacatctagc aatgtgagcg tcctgcagca gtttgccagt ggcctaaaga gccggaatga     180
ggaaaccagg gccaaagccg ccaaggagct ccagcactat gtcaccatgg aactccgaga     240
gatgagtcaa gaggagtcta ctcgcttcta tgaccaactg aaccatcaca ttttttgaatt     300
ggtttccagc tcagatgcca atgagaggaa aggtggcatc ttggccatag ctagcctcat     360
aggagtggaa ggtgggaatg ccacccgaat tggcagattt gccaactatc ttcggaacct     420
cctcccctcc aatgacccag ttgtcatgga aatggcatcc aaggccattg ccgtcttgc      480
catggcaggg gacactttta ccgctgagta cgtggaattt gaggtgaagc gagccctgga     540
atggctgggt gctgaccgca atgagggccg gagacatgca gctgtcctgg ttctccgtga     600
gctggccatc agcgtcccta ccttcttctt ccagcaagtg caacccttct ttgacaacat     660
ttttgtggcc gtgtgggacc caaacaggc catccgtgag ggagctgtag ccgcccttcg     720
tgcctgtctg attctcacaa cccagcgtga gccgaaggag atgcagaagc tcagtggta     780
```

-continued

| | |
|---|---|
| caggcacaca tttgaagaag cagagaaggg atttgatgag accttggcca aagagaaggg | 840 |
| catgaatcgg gatgatcgga tccatggagc cttgttgatc cttaacgagc tggtccgaat | 900 |
| cagcagcatg gagggagagc gtctgagaga agaaatggaa gaaatcacac agcagcagct | 960 |
| ggtacacgac aagtactgca aagatctcat gggcttcgga acaaaacctc gtcacattac | 1020 |
| ccccttcacc agtttccagg ctgtacagcc ccagcagtca aatgccttgg tggggctgct | 1080 |
| ggggtacagc tctcaccaag gcctcatggg atttgggacc tcccccagtc cagctaagtc | 1140 |
| caccctggtg gagagccggt gttgcagaga cttgatggag gagaaatttg atcaggtgtg | 1200 |
| ccagtgggtg ctgaaatgca ggaatagcaa gaactcgctg atccaaatga caatccttaa | 1260 |
| tttgttgccc cgcttggctg cattccgacc ttctgccttc acagatacc cagtatctcca | 1320 |
| agataccatg aaccatgtcc taagctgtgt caagaaggag aaggaacgta cagcggcctt | 1380 |
| ccaagccctg gggctacttt ctgtggctgt gaggtctgag tttaaggtct atttgcctcg | 1440 |
| cgtgctggac atcatccgag cggccctgcc cccaaaggac ttcgcccata agaggcagaa | 1500 |
| ggcaatgcag gtggacgcca cagtcttcac ttgcatcagc atgctggctc gagcaatggg | 1560 |
| gccaggcatc cagcaggata tcaaggagct gctggagccc atgctggcag tgggactaag | 1620 |
| ccctgccctc actgcagtgc tctacgacct gagccgtcag attccacagc taaagaagga | 1680 |
| cattcaagat gggctactga aaatgctgtc cctggtcctt atgcacaaac cccttcgcca | 1740 |
| cccaggcatg cccaagggcc tggcccatca gctggcctct cctggcctca cgaccctccc | 1800 |
| tgaggccagc gatgtgggca gcatcactct tgccctccga acgcttggca gctttgaatt | 1860 |
| tgaaggccac tctctgaccc aatttgttcg ccactgtgcg gatcatttcc tgaacagtga | 1920 |
| gcacaaggag atccgcatgg aggctgcccg cacctgctcc cgcctgctca cccctccat | 1980 |
| ccacctcatc agtggccatg ctcatgtggt tagccagacc gcagtgcaag tggtggcaga | 2040 |
| tgtgcttagc aaactgctcg tagttgggat aacagatcct gaccctgaca ttcgctactg | 2100 |
| tgtcttggcg tccctggacg agcgctttga tgcacacctg gcccaggcgg agaacttgca | 2160 |
| ggccttgttt gtggctctga atgaccaggt gtttgagatc cgggagctgg ccatctgcac | 2220 |
| tgtgggccga ctcagtagca tgaaccctgc cttttgtcatg cctttcctgc gcaagatgct | 2280 |
| catccagatt ttgacagagt tggagcacag tgggattgga agaatcaaag agcagagtgc | 2340 |
| ccgcatgctg gggcacctgg tctccaatgc cccccgactc atccgcccct acatggagcc | 2400 |
| tattctgaag gcattaattt tgaaactgaa agatccagac cctgatccaa acccaggtgt | 2460 |
| gatcaataat gtcctggcaa cataggaga attggcacag ttagtggcc tggaaatgag | 2520 |
| gaaatgggtt gatgaacttt ttattatcat catggacatg ctccaggatt cctctttgtt | 2580 |
| ggccaaaagg caggtggctc tgtggaccct gggacagttg gtggccagca ctggctatgt | 2640 |
| agtagagccc tacaggaagt accctacttt gcttgaggtg ctactgaatt ttctgaagac | 2700 |
| tgagcagaac cagggtacac gcagagaggc catccgtgtg ttagggcttt taggggcttt | 2760 |
| ggatccttac aagcacaaag tgaacattgg catgatagac cagtcccggg atgcctctgc | 2820 |
| tgtcagcctg tcagaatcca agtcaagtca ggattcctct gactatagca ctagtgaaat | 2880 |
| gctggtcaac atgggaaact tgcctctgga tgagttctac ccagctgtgt ccatggtggc | 2940 |
| cctgatgcgg atcttccgag accagtcact ctctcatcat cacaccatgg ttgtccaggc | 3000 |
| catcaccttc atcttcaagt ccctgggact caaatgtgtg cagttcctgc cccaggtcat | 3060 |
| gcccacgttc cttaatgtca ttcgagtctg tgatggggcc atccgggaat ttttgttcca | 3120 |
| gcagctggga atgttggtgt cctttgtgaa gagccacatc agaccttata tggatgaaat | 3180 |

-continued

| | |
|---|---|
| agtcaccctc atgagagaat tctgggtcat gaacacctca attcagagca cgatcattct | 3240 |
| tctcattgag caaattgtgg tagctcttgg gggtgaattt aagctctacc tgccccagct | 3300 |
| gatcccacac atgctgcgtg tcttcatgca tgacaacagc ccaggccgca ttgtctctat | 3360 |
| caagttactg gctgcaatcc agctgtttgg cgccaacctg gatgactacc tgcatttact | 3420 |
| gctgcctcct attgttaagt tgtttgatgc ccctgaagct ccactgccat ctcgaaaggc | 3480 |
| agcgctagag actgtggacc gcctgacgga gtccctggat ttcactgact atgcctcccg | 3540 |
| gatcattcac cctattgttc aacactgga ccagagccca gaactgcgct ccacagccat | 3600 |
| ggacacgctg tcttcacttg tttttcagct ggggaagaag taccaaattt tcattccaat | 3660 |
| ggtgaataaa gttctggtgc gacaccgaat caatcatcag cgctatgatg tgctcatctg | 3720 |
| cagaattgtc aagggataca cacttgctga tgaagaggag gatcctttga tttaccagca | 3780 |
| tcggatgctt aggagtggcc aaggggatgc attggctagt ggaccagtgg aaacaggacc | 3840 |
| catgaagaaa ctgcacgtca gcaccatcaa cctccaaaag gcctgggggcg ctgccaggag | 3900 |
| ggtctccaaa gatgactggc tggaatggct gagacggctg agcctggagc tgctgaagga | 3960 |
| ctcatcatcg ccctccctgc gctcctgctg ggccctggca caggcctaca acccgatggc | 4020 |
| cagggatctc ttcaatgctg catttgtgtc ctgctggtct gaactgaatg aagatcaaca | 4080 |
| ggatgagctc atcagaagca tcgagttggc cctcacctca caagacatcg ctgaagtcac | 4140 |
| acagaccctc ttaaacttgg ctgaattcat ggaacacagt gacaagggcc ccctgccact | 4200 |
| gagagatgac aatggcattg ttctgctggg tgagagagct gccaagtgcc gagcatatgc | 4260 |
| caaagcacta cactacaaag aactggagtt ccagaaaggc cccaccctg ccattctaga | 4320 |
| atctctcatc agcattaata ataagctaca gcagccggag gcagcggccg gagtgttaga | 4380 |
| atatgccatg aaacactttg gagagctgga gatccaggct acctggtatg agaaactgca | 4440 |
| cgagtgggag gatgcccttg tggcctatga caagaaaatg gacaccaaca aggacgaccc | 4500 |
| agagctgatg ctgggccgca tgcgctgcct cgaggccttg ggggaatggg gtcaactcca | 4560 |
| ccagcagtgc tgtgaaaagt ggaccctggt taatgatgag acccaagcca agatggcccg | 4620 |
| gatggctgct gcagctgcat ggggtttagg tcagtgggac agcatggaag aatacacctg | 4680 |
| tatgatccct cgggacaccc atgatggggc attttataga gctgtgctgg cactgcatca | 4740 |
| ggacctcttc tccttggcac aacagtgcat tgacaaggcc agggacctgc tggatgctga | 4800 |
| attaactgca atggcaggag agagttacag tcgggcatat ggggccatgg tttcttgcca | 4860 |
| catgctgtcc gagctggagg aggttatcca gtacaaactt gtccccgagc gacgagagat | 4920 |
| catccgccag atctggtggg agagactgca gggctgccag cgtatcgtag aggactggca | 4980 |
| gaaaatcctt atggtgcggt cccttgtggt cagccctcat gaagacatga aacctggct | 5040 |
| caagtatgca agcctgtgcg gcaagagtgg caggctggct cttgctcata aaactttagt | 5100 |
| gttgctcctg ggagttgatc cgtctcggca acttgaccat cctctgccaa cagttcaccc | 5160 |
| tcaggtgacc tatgcctaca tgaaaaacat gtggaagagt gcccgcaaga tcgatgcctt | 5220 |
| ccagcacatg cagcattttg tccagaccat gcagcaacag gcccagcatg ccatcgctac | 5280 |
| tgaggaccag cagcataagc aggaactgca caagctcatg gcccgatgct tcctgaaact | 5340 |
| tggagagtgg cagctgaatc tacagggcat caatgagagc acaatccca aagtgctgca | 5400 |
| gtactacagc gccgccacag agcacgaccg cagctggtac aaggcctggc atgcgtgggc | 5460 |
| agtgatgaac ttcgaagctg tgctacacta caaacatcag aaccaagccc gcatgagaa | 5520 |
| gaagaaactg cgtcatgcca gcggggccaa catcaccaac gccaccactg ccgccaccac | 5580 |

```
ggccgccact gccaccacca ctgccagcac cgagggcagc aacagtgaga gcgaggccga    5640
gagcaccgag aacagcccca ccccatcgcc gctgcagaag aaggtcactg aggatctgtc    5700
caaaaccctc ctgatgtaca cggtgcctgc cgtccagggc ttcttccgtt ccatctcctt    5760
gtcacgaggc aacaacctcc aggatacact cagagttctc accttatggt ttgattatgg    5820
tcactggcca gatgtcaatg aggccttagt ggagggggtg aaagccatcc agattgatac    5880
ctggctacag gttataccte agctcattgc aagaattgat acgcccagac ccttggtggg    5940
acgtctcatt caccagcttc tcacagacat tggtcggtac cacccccagg ccctcatcta    6000
cccactgaca gtggcttcta agtctaccac gacagcccgg cacaatgcag ccaacaagat    6060
tctgaagaac atgtgtgagc acagcaacac cctggtccag caggccatga tggtgagcga    6120
ggagctgatc cgagtggcca tcctctggca tgagatgtgg catgaaggcc tggaagaggc    6180
atctcgtttg tactttgggg aaaggaacgt gaaaggcatg tttgaggtgc tggagcccttt   6240 gcatgctatg atggaacggg ccccccagac tctgaaggaa acatcccttta atcaggccta    6300 tggtcgagat ttaatggagg cccaagagtg gtgcaggaag tacatgaaat cagggaatgt    6360
caaggacctc acccaagcct gggacctcta ttatcatgtg ttccgacgaa tctcaaagca    6420
gctgcctcag ctcacatcct tagagctgca atatgtttcc ccaaaacttc tgatgtgccg    6480
ggaccttgaa ttggctgtgc caggaacata tgacccgaac cagccaatca ttcgcattca    6540
gtccatagca ccgtctttgc aagtcatcac atccaagcag aggccccgga aattgacact    6600
tatgggcagc aacggacatg agtttgtttt ccttctaaaa ggccatgaag atctgcgcca    6660
ggatgagcgt gtgatgcagc tcttcggcct ggttaacacc cttctggcca atgacccaac    6720
atctcttcgg aaaaacctca gcatccgag atacgctgtc atcccttat cgaccaactc      6780 gggcctcatt ggctgggttc cccactgtga cacactgcac gccctcatcc gggactacag    6840
ggagaagaag aagatccttc tcaacatcga gcatcgcatc atgttgcgga tggctccgga    6900
ctatgaccac ttgactctga tgcagaaggt ggaggtgttt gagcatgccg tcaataatac    6960
agctggggac gacctggcca agctgctgtg gctgaaaagc cccagctccg aggtgtggtt    7020
tgaccgaaga accaattata cccgttcttt agcggtcatg tcaatggttg ggtatatttt    7080
aggcctggga gatagacacc catccaacct gatgctggac cgtctgagtg ggaagatcct    7140
gcacattgac tttggggact gctttgaggt tgctatgacc cgagagaagt ttccagagaa    7200
gattccattt agactaacaa gaatgttgac caatgctatg gaggttacag gcctggatgg    7260
caactacaga atcacatgcc acacagtgat ggaggtgctg cgagagcaca ggacagtgt    7320 catggccgtg ctggaagcct ttgtctatga cccccttgctg aactggaggc tgatggacac    7380
aaataccaaa ggcaacaagc gatcccgaac gaggacggat tcctactctg ctggccagtc    7440
agtcgaaatt ttggacggtg tggaacttgg agagccagcc cataagaaaa cggggaccac    7500
agtgccagaa tctattcatt cttttcattgg agacggtttg gtgaaaccag aggccctaaa    7560
taagaaagct atccagatta ttaacagggt tcgagataag ctcactggtc gggacttctc    7620
tcatgatgac actttggatg ttccaacgca agttgagctg ctcatcaaac aagcgacatc    7680
ccatgaaaac ctctgccagt gctatattgg ctggtgccct ttctggtaac tggaggccca    7740
gatgtgccca tcacgttttt tctgaggctt ttgtacttta gtaaatgctt ccactaaact    7800
gaaaccatgg tgagaaagtt tgactttgtt aaatattttg aaatgtaaat gaaaagaagt    7860
actgtatatt aaaagttggt ttgaaccaac tttctagctg ctgttgaaga atatattgtc    7920
agaaacacaa ggcttgattt ggt                                            7943
```

-continued

<210> SEQ ID NO 4
<211> LENGTH: 2549
<212> TYPE: PRT
<213> ORGANISM: Homo sapiens

<400> SEQUENCE: 4

Met Leu Gly Thr Gly Pro Ala Ala Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
    370                 375                 380

```
Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
            405                 410                 415

Met Asn His Val Leu Ser Cys Val Lys Lys Glu Lys Glu Arg Thr Ala
        420                 425                 430

Ala Phe Gln Ala Leu Gly Leu Leu Ser Val Ala Val Arg Ser Glu Phe
    435                 440                 445

Lys Val Tyr Leu Pro Arg Val Leu Asp Ile Ile Arg Ala Ala Leu Pro
450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
            485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
    515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
            565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
    595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Ala Asp Val Leu
            645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
            675                 680                 685

Gln Ala Glu Asn Leu Gln Ala Leu Phe Val Ala Leu Asn Asp Gln Val
    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
            725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
    755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
            805                 810                 815
```

-continued

Val Asp Glu Leu Phe Ile Ile Ile Met Asp Met Leu Gln Asp Ser Ser
         820                 825                 830

Leu Leu Ala Lys Arg Gln Val Ala Leu Trp Thr Leu Gly Gln Leu Val
         835                 840                 845

Ala Ser Thr Gly Tyr Val Val Glu Pro Tyr Arg Lys Tyr Pro Thr Leu
         850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                 885                 890                 895

Tyr Lys His Lys Val Asn Ile Gly Met Ile Asp Gln Ser Arg Asp Ala
             900                 905                 910

Ser Ala Val Ser Leu Ser Glu Ser Lys Ser Ser Gln Asp Ser Ser Asp
             915                 920                 925

Tyr Ser Thr Ser Glu Met Leu Val Asn Met Gly Asn Leu Pro Leu Asp
         930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                 965                 970                 975

Phe Ile Phe Lys Ser Leu Gly Leu Lys Cys Val Gln Phe Leu Pro Gln
             980                 985                 990

Val Met Pro Thr Phe Leu Asn Val Ile Arg Val Cys Asp Gly Ala Ile
             995                1000                1005

Arg Glu Phe Leu Phe Gln Gln Leu Gly Met Leu Val Ser Phe Val
     1010                1015                1020

Lys Ser His Ile Arg Pro Tyr Met Asp Glu Ile Val Thr Leu Met
     1025                1030                1035

Arg Glu Phe Trp Val Met Asn Thr Ser Ile Gln Ser Thr Ile Ile
     1040                1045                1050

Leu Leu Ile Glu Gln Ile Val Ala Leu Gly Gly Glu Phe Lys
     1055                1060                1065

Leu Tyr Leu Pro Gln Leu Ile Pro His Met Leu Arg Val Phe Met
     1070                1075                1080

His Asp Asn Ser Pro Gly Arg Ile Val Ser Ile Lys Leu Leu Ala
     1085                1090                1095

Ala Ile Gln Leu Phe Gly Ala Asn Leu Asp Asp Tyr Leu His Leu
     1100                1105                1110

Leu Leu Pro Pro Ile Val Lys Leu Phe Asp Ala Pro Glu Ala Pro
     1115                1120                1125

Leu Pro Ser Arg Lys Ala Ala Leu Glu Thr Val Asp Arg Leu Thr
     1130                1135                1140

Glu Ser Leu Asp Phe Thr Asp Tyr Ala Ser Arg Ile Ile His Pro
     1145                1150                1155

Ile Val Arg Thr Leu Asp Gln Ser Pro Glu Leu Arg Ser Thr Ala
     1160                1165                1170

Met Asp Thr Leu Ser Ser Leu Val Phe Gln Leu Gly Lys Lys Tyr
     1175                1180                1185

Gln Ile Phe Ile Pro Met Val Asn Lys Val Leu Val Arg His Arg
     1190                1195                1200

Ile Asn His Gln Arg Tyr Asp Val Leu Ile Cys Arg Ile Val Lys
     1205                1210                1215

Gly Tyr Thr Leu Ala Asp Glu Glu Glu Asp Pro Leu Ile Tyr Gln

-continued

```
            1220             1225             1230
His Arg Met Leu Arg Ser Gly Gln Gly Asp Ala Leu Ala Ser Gly
        1235             1240             1245

Pro Val Glu Thr Gly Pro Met Lys Lys Leu His Val Ser Thr Ile
    1250             1255             1260

Asn Leu Gln Lys Ala Trp Gly Ala Arg Arg Val Ser Lys Asp
    1265             1270             1275

Asp Trp Leu Glu Trp Leu Arg Arg Leu Ser Leu Glu Leu Leu Lys
    1280             1285             1290

Asp Ser Ser Ser Pro Ser Leu Arg Ser Cys Trp Ala Leu Ala Gln
    1295             1300             1305

Ala Tyr Asn Pro Met Ala Arg Asp Leu Phe Asn Ala Ala Phe Val
    1310             1315             1320

Ser Cys Trp Ser Glu Leu Asn Glu Asp Gln Gln Asp Glu Leu Ile
    1325             1330             1335

Arg Ser Ile Glu Leu Ala Leu Thr Ser Gln Asp Ile Ala Glu Val
    1340             1345             1350

Thr Gln Thr Leu Leu Asn Leu Ala Glu Phe Met Glu His Ser Asp
    1355             1360             1365

Lys Gly Pro Leu Pro Leu Arg Asp Asp Asn Gly Ile Val Leu Leu
    1370             1375             1380

Gly Glu Arg Ala Ala Lys Cys Arg Ala Tyr Ala Lys Ala Leu His
    1385             1390             1395

Tyr Lys Glu Leu Glu Phe Gln Lys Gly Pro Thr Pro Ala Ile Leu
    1400             1405             1410

Glu Ser Leu Ile Ser Ile Asn Asn Lys Leu Gln Gln Pro Glu Ala
    1415             1420             1425

Ala Ala Gly Val Leu Glu Tyr Ala Met Lys His Phe Gly Glu Leu
    1430             1435             1440

Glu Ile Gln Ala Thr Trp Tyr Glu Lys Leu His Glu Trp Glu Asp
    1445             1450             1455

Ala Leu Val Ala Tyr Asp Lys Lys Met Asp Thr Asn Lys Asp Asp
    1460             1465             1470

Pro Glu Leu Met Leu Gly Arg Met Arg Cys Leu Glu Ala Leu Gly
    1475             1480             1485

Glu Trp Gly Gln Leu His Gln Gln Cys Cys Glu Lys Trp Thr Leu
    1490             1495             1500

Val Asn Asp Glu Thr Gln Ala Lys Met Ala Arg Met Ala Ala Ala
    1505             1510             1515

Ala Ala Trp Gly Leu Gly Gln Trp Asp Ser Met Glu Glu Tyr Thr
    1520             1525             1530

Cys Met Ile Pro Arg Asp Thr His Asp Gly Ala Phe Tyr Arg Ala
    1535             1540             1545

Val Leu Ala Leu His Gln Asp Leu Phe Ser Leu Ala Gln Gln Cys
    1550             1555             1560

Ile Asp Lys Ala Arg Asp Leu Leu Asp Ala Glu Leu Thr Ala Met
    1565             1570             1575

Ala Gly Glu Ser Tyr Ser Arg Ala Tyr Gly Ala Met Val Ser Cys
    1580             1585             1590

His Met Leu Ser Glu Leu Glu Glu Val Ile Gln Tyr Lys Leu Val
    1595             1600             1605

Pro Glu Arg Arg Glu Ile Ile Arg Gln Ile Trp Trp Glu Arg Leu
    1610             1615             1620
```

-continued

Gln Gly Cys Gln Arg Ile Val Glu Asp Trp Gln Lys Ile Leu Met
1625                1630                1635

Val Arg Ser Leu Val Val Ser Pro His Glu Asp Met Arg Thr Trp
1640                1645                1650

Leu Lys Tyr Ala Ser Leu Cys Gly Lys Ser Gly Arg Leu Ala Leu
1655                1660                1665

Ala His Lys Thr Leu Val Leu Leu Leu Gly Val Asp Pro Ser Arg
1670                1675                1680

Gln Leu Asp His Pro Leu Pro Thr Val His Pro Gln Val Thr Tyr
1685                1690                1695

Ala Tyr Met Lys Asn Met Trp Lys Ser Ala Arg Lys Ile Asp Ala
1700                1705                1710

Phe Gln His Met Gln His Phe Val Gln Thr Met Gln Gln Gln Ala
1715                1720                1725

Gln His Ala Ile Ala Thr Glu Asp Gln Gln His Lys Gln Glu Leu
1730                1735                1740

His Lys Leu Met Ala Arg Cys Phe Leu Lys Leu Gly Glu Trp Gln
1745                1750                1755

Leu Asn Leu Gln Gly Ile Asn Glu Ser Thr Ile Pro Lys Val Leu
1760                1765                1770

Gln Tyr Tyr Ser Ala Ala Thr Glu His Asp Arg Ser Trp Tyr Lys
1775                1780                1785

Ala Trp His Ala Trp Ala Val Met Asn Phe Glu Ala Val Leu His
1790                1795                1800

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830

Thr Ala Ala Thr Ala Thr Thr Ala Ser Thr Glu Gly Ser Asn
1835                1840                1845

Ser Glu Ser Glu Ala Glu Ser Thr Glu Asn Ser Pro Thr Pro Ser
1850                1855                1860

Pro Leu Gln Lys Lys Val Thr Glu Asp Leu Ser Lys Thr Leu Leu
1865                1870                1875

Met Tyr Thr Val Pro Ala Val Gln Gly Phe Phe Arg Ser Ile Ser
1880                1885                1890

Leu Ser Arg Gly Asn Asn Leu Gln Asp Thr Leu Arg Val Leu Thr
1895                1900                1905

Leu Trp Phe Asp Tyr Gly His Trp Pro Asp Val Asn Glu Ala Leu
1910                1915                1920

Val Glu Gly Val Lys Ala Ile Gln Ile Asp Thr Trp Leu Gln Val
1925                1930                1935

Ile Pro Gln Leu Ile Ala Arg Ile Asp Thr Pro Arg Pro Leu Val
1940                1945                1950

Gly Arg Leu Ile His Gln Leu Leu Thr Asp Ile Gly Arg Tyr His
1955                1960                1965

Pro Gln Ala Leu Ile Tyr Pro Leu Thr Val Ala Ser Lys Ser Thr
1970                1975                1980

Thr Thr Ala Arg His Asn Ala Ala Asn Lys Ile Leu Lys Asn Met
1985                1990                1995

Cys Glu His Ser Asn Thr Leu Val Gln Gln Ala Met Met Val Ser
2000                2005                2010

Glu Glu Leu Ile Arg Val Ala Ile Leu Trp His Glu Met Trp His
2015                2020                2025

-continued

| | | | | | | | | | | |
|---|---|---|---|---|---|---|---|---|---|---|
|Glu|Gly|Leu|Glu|Glu|Ala|Ser|Arg|Leu|Tyr|Phe|Gly|Glu|Arg|Asn|
| |2030| | | |2035| | | |2040| | | | | |

Val Lys Gly Met Phe Glu Val Leu Glu Pro Leu His Ala Met Met
    2045            2050            2055

Glu Arg Gly Pro Gln Thr Leu Lys Glu Thr Ser Phe Asn Gln Ala
    2060            2065            2070

Tyr Gly Arg Asp Leu Met Glu Ala Gln Glu Trp Cys Arg Lys Tyr
    2075            2080            2085

Met Lys Ser Gly Asn Val Lys Asp Leu Thr Gln Ala Trp Asp Leu
    2090            2095            2100

Tyr Tyr His Val Phe Arg Arg Ile Ser Lys Gln Leu Pro Gln Leu
    2105            2110            2115

Thr Ser Leu Glu Leu Gln Tyr Val Ser Pro Lys Leu Leu Met Cys
    2120            2125            2130

Arg Asp Leu Glu Leu Ala Val Pro Gly Thr Tyr Asp Pro Asn Gln
    2135            2140            2145

Pro Ile Ile Arg Ile Gln Ser Ile Ala Pro Ser Leu Gln Val Ile
    2150            2155            2160

Thr Ser Lys Gln Arg Pro Arg Lys Leu Thr Leu Met Gly Ser Asn
    2165            2170            2175

Gly His Glu Phe Val Phe Leu Leu Lys Gly His Glu Asp Leu Arg
    2180            2185            2190

Gln Asp Glu Arg Val Met Gln Leu Phe Gly Leu Val Asn Thr Leu
    2195            2200            2205

Leu Ala Asn Asp Pro Thr Ser Leu Arg Lys Asn Leu Ser Ile Gln
    2210            2215            2220

Arg Tyr Ala Val Ile Pro Leu Ser Thr Asn Ser Gly Leu Ile Gly
    2225            2230            2235

Trp Val Pro His Cys Asp Thr Leu His Ala Leu Ile Arg Asp Tyr
    2240            2245            2250

Arg Glu Lys Lys Lys Ile Leu Leu Asn Ile Glu His Arg Ile Met
    2255            2260            2265

Leu Arg Met Ala Pro Asp Tyr Asp His Leu Thr Leu Met Gln Lys
    2270            2275            2280

Val Glu Val Phe Glu His Ala Val Asn Asn Thr Ala Gly Asp Asp
    2285            2290            2295

Leu Ala Lys Leu Leu Trp Leu Lys Ser Pro Ser Ser Glu Val Trp
    2300            2305            2310

Phe Asp Arg Arg Thr Asn Tyr Thr Arg Ser Leu Ala Val Met Ser
    2315            2320            2325

Met Val Gly Tyr Ile Leu Gly Leu Gly Asp Arg His Pro Ser Asn
    2330            2335            2340

Leu Met Leu Asp Arg Leu Ser Gly Lys Ile Leu His Ile Asp Phe
    2345            2350            2355

Gly Asp Cys Phe Glu Val Ala Met Thr Arg Glu Lys Phe Pro Glu
    2360            2365            2370

Lys Ile Pro Phe Arg Leu Thr Arg Met Leu Thr Asn Ala Met Glu
    2375            2380            2385

Val Thr Gly Leu Asp Gly Asn Tyr Arg Ile Thr Cys His Thr Val
    2390            2395            2400

Met Glu Val Leu Arg Glu His Lys Asp Ser Val Met Ala Val Leu
    2405            2410            2415

Glu Ala Phe Val Tyr Asp Pro Leu Leu Asn Trp Arg Leu Met Asp

```
            2420                2425                2430
Thr Asn Thr Lys Gly Asn Lys Arg Ser Arg Thr Arg Thr Asp Ser
        2435                2440                2445
Tyr Ser Ala Gly Gln Ser Val Glu Ile Leu Asp Gly Val Glu Leu
        2450                2455                2460
Gly Glu Pro Ala His Lys Lys Thr Gly Thr Thr Val Pro Glu Ser
        2465                2470                2475
Ile His Ser Phe Ile Gly Asp Gly Leu Val Lys Pro Glu Ala Leu
        2480                2485                2490
Asn Lys Lys Ala Ile Gln Ile Ile Asn Arg Val Arg Asp Lys Leu
        2495                2500                2505
Thr Gly Arg Asp Phe Ser His Asp Asp Thr Leu Asp Val Pro Thr
        2510                2515                2520
Gln Val Glu Leu Leu Ile Lys Gln Ala Thr Ser His Glu Asn Leu
        2525                2530                2535
Cys Gln Cys Tyr Ile Gly Trp Cys Pro Phe Trp
        2540                2545

<210> SEQ ID NO 5
<211> LENGTH: 22
<212> TYPE: DNA
<213> ORGANISM: Artificial
<220> FEATURE:
<223> OTHER INFORMATION: N-terminal primer N1

<400> SEQUENCE: 5
atgcttggaa ccggacctgc cg                                              22

<210> SEQ ID NO 6
<211> LENGTH: 23
<212> TYPE: DNA
<213> ORGANISM: Artificial
<220> FEATURE:
<223> OTHER INFORMATION: FATN domain primer C3

<400> SEQUENCE: 6
tttggacaga tcctcagtga cct                                             23

<210> SEQ ID NO 7
<211> LENGTH: 22
<212> TYPE: DNA
<213> ORGANISM: Artificial
<220> FEATURE:
<223> OTHER INFORMATION: Extreme N1 Primer

<400> SEQUENCE: 7
atgcttggaa ccggacctgc cg                                              22

<210> SEQ ID NO 8
<211> LENGTH: 18
<212> TYPE: DNA
<213> ORGANISM: Artificial
<220> FEATURE:
<223> OTHER INFORMATION: C1 Primer

<400> SEQUENCE: 8
ttaccagaaa gggcacca                                                   18

<210> SEQ ID NO 9
<211> LENGTH: 97
<212> TYPE: DNA
<213> ORGANISM: Homo sapiens
<220> FEATURE:
```

```
<223> OTHER INFORMATION: Amplified fragment from PCR of human MCF7,
      Hek293 and HEP2G cell lines

<400> SEQUENCE: 9
atgcttggaa ccggacctgc cgccgccacc accgctgcca ccacatctag caatgtgagc      60
gtcctgcaga agaaggtcac tgaggatctg tccaaaa                              97

<210> SEQ ID NO 10
<211> LENGTH: 32
<212> TYPE: PRT
<213> ORGANISM: Homo sapiens
<220> FEATURE:
<223> OTHER INFORMATION: Translated sequence of Amplified fragment from
      PCR of human MCF7, Hek293 and HEP2G cell lines

<400> SEQUENCE: 10

Met Leu Gly Thr Gly Pro Ala Ala Ala Thr Thr Ala Ala Thr Thr Ser
1               5                   10                  15

Ser Asn Val Ser Val Leu Gln Lys Lys Val Thr Glu Asp Leu Ser Lys
                20                  25                  30
```